(12) United States Patent
Bandura et al.

(10) Patent No.: US 10,436,698 B2
(45) Date of Patent: *Oct. 8, 2019

(54) MASS SPECTROMETRY BASED MULTI-PARAMETRIC PARTICLE ANALYZER

(71) Applicant: Fluidigm Corporation, South San Francisco, CA (US)

(72) Inventors: Dmitry R. Bandura, Ontario (CA); Vladimir I. Baranov, Ontario (CA); Scott D. Tanner, Ontario (CA)

(73) Assignee: FLUIDIGM CORPORATION, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,570

(22) Filed: Dec. 21, 2018

(65) Prior Publication Data

US 2019/0195771 A1    Jun. 27, 2019

Related U.S. Application Data

(60) Continuation of application No. 15/888,871, filed on Feb. 5, 2018, now Pat. No. 10,180,386, which is a
(Continued)

(51) Int. Cl.
*G01N 15/14*    (2006.01)
*H01J 49/00*    (2006.01)
(Continued)

(52) U.S. Cl.
CPC ........ *G01N 15/1404* (2013.01); *H01J 49/004* (2013.01); *H01J 49/04* (2013.01);
(Continued)

(58) Field of Classification Search
None
See application file for complete search history.

(56) References Cited

U.S. PATENT DOCUMENTS 4,022,876 A    5/1977  Anabar
4,205,952 A    6/1980  Cais
(Continued)

FOREIGN PATENT DOCUMENTS

WO    9714028 A2    4/1997
WO    9919515 A1    4/1999
(Continued)

OTHER PUBLICATIONS

Nomizu et al., "Determination of Calcium Content in Individual Biological Cells by Inductively Coupled Plasma Atomic Emission Spectrometry," Anal. Chem. 1994, vol. 66, pp. 3000-3004.
(Continued)

*Primary Examiner* — Andrew Smyth
(74) *Attorney, Agent, or Firm* — Kilpatrick Townsend & Stockton LLP

(57) ABSTRACT

An analytical instrument has a sample introduction system for generating a stream of particles from a sample. An ionization system atomizes and ionizes particles in the stream as they are received. The instrument has an ion pretreatment system and a mass analyzer. The ion pretreatment system is adapted to transport ions generated by the ionization system to the mass analyzer. The mass analyzer is adapted measure the amount of at least one element in individual particles from the stream by performing mass analysis on the ions from the atomized particles. The instrument can be adapted to measure the amount of many different tags, for example at least five different tags, at the same time to facilitate multi-parametric analysis of cells and other particles.

6 Claims, 11 Drawing Sheets

Related U.S. Application Data continuation of application No. 13/294,799, filed on Nov. 11, 2011, now Pat. No. 9,952,134, which is a continuation of application No. 12/332,812, filed on Dec. 11, 2008, now abandoned, which is a division of application No. 11/089,023, filed on Mar. 25, 2005, now Pat. No. 7,479,630.

(60) Provisional application No. 60/555,952, filed on Mar. 25, 2004.

(51) Int. Cl.
*H01J 49/04* (2006.01)
*G01N 15/00* (2006.01)

(52) U.S. Cl.
CPC .. *H01J 49/0431* (2013.01); *G01N 2015/0065* (2013.01); *G01N 2458/15* (2013.01)

(56) References Cited

U.S. PATENT DOCUMENTS

| | | | |
|---|---|---|---|
| 4,454,233 A | 6/1984 | Wang | |
| 4,499,052 A | 2/1985 | Fulwyler | |
| 4,543,439 A | 9/1985 | Frackelton, Jr. et al. | |
| 4,717,655 A | 1/1988 | Fulwyler | |
| 5,073,497 A | 12/1991 | Schwartz | |
| 5,073,498 A | 12/1991 | Schwartz et al. | |
| 5,194,300 A | 3/1993 | Cheung | |
| 5,585,241 A | 12/1996 | Lindmo | |
| 5,723,218 A | 3/1998 | Haugland et al. | |
| 5,736,330 A | 4/1998 | Fulton | |
| 6,057,107 A | 5/2000 | Fulton | |
| 6,140,638 A | 10/2000 | Tanner et al. | |
| 6,177,266 B1 | 1/2001 | Krishnamurthy et al. | |
| 6,242,735 B1 | 6/2001 | Li et al. | |
| 6,514,295 B1 | 2/2003 | Chandler et al. | |
| 6,524,793 B1 | 2/2003 | Chandler et al. | |
| 6,599,331 B2 | 7/2003 | Chandler et al. | |
| 6,632,528 B1 | 10/2003 | Clough | |
| 6,750,449 B2 | 6/2004 | Marcus | |
| 6,815,212 B2 | 11/2004 | Ness et al. | |
| 6,939,720 B2 | 9/2005 | Chandler et al. | |
| 6,943,346 B2 | 9/2005 | Tan | |
| 6,949,739 B2 | 9/2005 | Franzen | |
| 7,135,296 B2 | 11/2006 | Baranov et al. | |
| 7,198,900 B2 | 4/2007 | Woudenberg et al. | |
| 7,410,763 B2 | 8/2008 | Su et al. | |
| 7,479,630 B2 | 1/2009 | Bandura et al. | |
| 7,494,776 B2 | 2/2009 | Wallace et al. | |
| 7,700,295 B2 | 4/2010 | Baranov et al. | |
| 7,767,407 B2 | 8/2010 | Baranov et al. | |
| 7,901,628 B2 | 3/2011 | Yamamoto | |
| 9,952,134 B2 | 4/2018 | Bandura et al. | |
| 10,180,386 B2 * | 1/2019 | Bandura | G01N 15/1404 |
| 2002/0003210 A1 | 1/2002 | Marcus | |
| 2002/0028434 A1 | 3/2002 | Goix et al. | |
| 2002/0086441 A1 * | 7/2002 | Baranov | G01N 33/532 436/518 |
| 2002/0173454 A1 * | 11/2002 | Rosen | C07K 14/47 435/6.16 |
| 2003/0028981 A1 | 2/2003 | Chandler et al. | |
| 2003/0077595 A1 * | 4/2003 | Van Ness | C12Q 1/6872 435/6.12 |
| 2004/0011953 A1 | 1/2004 | Chen et al. | |
| 2004/0053052 A1 | 3/2004 | Chandler et al. | |
| 2004/0072250 A1 | 4/2004 | Baranov et al. | |
| 2004/0126277 A1 | 7/2004 | Yamamoto | |
| 2004/0129876 A1 | 7/2004 | Franzen | |
| 2005/0118574 A1 | 6/2005 | Chandler et al. | |
| 2005/0164261 A1 | 9/2005 | Chandler et al. | |
| 2005/0202469 A1 | 9/2005 | Chandler et al. | |
| 2005/0218319 A1 | 10/2005 | Bandura et al. | |
| 2005/0260676 A1 | 11/2005 | Chandler et al. | |
| 2009/0001264 A1 | 1/2009 | Yamamoto | |
| 2018/0195948 A1 | 7/2018 | Bandura et al. | |

FOREIGN PATENT DOCUMENTS

| | | |
|---|---|---|
| WO | 02054075 A1 | 7/2002 |
| WO | 2005003767 A2 | 1/2005 |
| WO | 2005093784 A1 | 10/2005 |

OTHER PUBLICATIONS

Bazilio & Weinrich, The Easy Guide to: Inductively Coupled Plasma-Mass Spectrometry (ICP-MS), 2012, http://www.ecs.umass.edu/eve/facilities/equipment/ICPMS/ICPMS%20quick%20guide.pdf.

Thomas "Practical guide to ICP-MS", 2004, Marcel Dekker, Inc., pp. 1-324.

Stewart and Olesik, Time-Resolved Measurements with Single Droplet Introduction to Investigate Space-Charge Effects in Plasma Mass Spectrometry, J. Am. Soc. Mass Spectrom., 1999, v. 10, pp. 159-174.

Kindness, et al. ("Two-Dimensional Mapping of Copper and Zinc in Liver Sections by Laser Ablation-Inductively Coupled Plasma Mass Spectrometry," Clinical Chemistry, vol. 49, No. 11, 2003, pp. 1916-1923).

Bandura et al., "Mass Cytometry: Technique for Real Time Single Cell Multitarget Immunoassay Based on Inductively Coupled Plasma Time-of-Flight Mass Spectrometry", Anal. Chem., 2009, v. 81, pp. 6813-6822.

Boulyga et al., "Performance of ICP-MS with Hexapole Collision Cell and Application for Determination of Trace Elements in Bio-Assays", Microchim. Acta, 2001, v. 137, pp. 93-103.

Nomizu et al., "Determination of zinc in individual airborne particles by inductively coupled plasma mass spectrometry with digital signal processing", J. Anal. At. Spectrom., 2002, v. 17, pp. 592-595.

Baumgarth and Roederer, "A practical approach to multicolor flow cytometry for immunophenotyping", J.Immunol. Methods, 200, v. 243, pp. 77-97.

Katayama et al. "Improvement of in-gel digestion protocol for peptide mass fingerprinting by matrix-assisted laser desorption ionization time-of-flight mass spectrometry", Rapid Commun. Mass Spectrom., 2001, v. 15, pp. 1416-1421.

Thomas, "A Beginner's Guide to ICP-MS", Parts I-XI, Spectroscopy, 2001-2002, v. 16-17, not all pages.

Chow et al. "Measurement of MAP Kinase Activation by Flow Cytometry Using Phospho-Specific Antibodies to MEK and ERK: Potential for Pharmacodynamic Monitoring of Signal Transduction Inhibitors", Cytometry, 2001, v. 46, pp. 72-78.

"A flow cytometry revolution", Nature Methods l vol. 8 No. 7 l Jul. 2011 l 531.

Thomas, "A Beginner's Guide to ICP-MS. Part VIII—Mass Analyzers: Time-of-Flight Technology", Spectroscopy Tutorial, Spectroscopy, 2002, v. 17, No. 1, pp. 37-41.

Alduncin, J.A., et al., "Miniemulsion Polymerization Using Oil-Soluble Initiators," 1994, Macromol, 27, pp. 2256-2261.

Alduncin, J.A., et al., "Molecular-Weight Distributions in the Miniemulsion Polymerization of Styrene Initiated by Oil-Soluble Initiators," 1994, Polymer, 35, pp. 3758-3765.

Antonietti, M., et al., "Polyreactions in Miniemulsions," 2002, Prog. Polym. Sci., 27, pp. 689-757.

Baranov, V.I., "ICP-MS as an Elemental Detector in Immunoassays, Speciation Without Chromatography," 2001, European winter Conference on Plasma Spectrochemistry, Hafjell, Norway, Winter 2001, Book of Abstracts, pp. 85.

Baranov et al., "A Sensitive and Quantitative Element-Tagged Immunoassay with ICPMS Detection," Anal. Chem., 2002, v. 74, pp. 1629-1636.

Baranov, V.I., et al., "The Potential for Element Analysis in Biotechnology," 2002, J Anal at Spectrom, 17:1148-1152.

Bartel, et al., "Isolation of New Ribozymes From a Large Pool of Random Sequences," 1993, Science, 261:1411-1418.

(56) References Cited

OTHER PUBLICATIONS

Bechthold, N., et al., "Miniemulsion Polymerization: Applications and New Materials," 2000, Macromol Symp, 151 : 549-555.
Blythe, P.J., et al., "Miniemulsion Polymerization of Styrene Using the Oil-Soluble Initiator AMBN," 1999, J Polym Sci, Part A, 37:4449-4457.
Brown, W.B., et al., "Extraction of the Lanthanides with Acetylacetone," 1960, J Inorg Nucl Chem, 13:119-124.
Chern, C.S., et al., "Particle nucleation loci in styrene miniemulsion polymerization using alkyl methacrylates as the reactive cosuliactant," 1998, Macromol Chem Phys, 199:1315-1322.
Chern, C.S., et al., "Kinetics of styrene miniemulsion polymerization stabilized by nonionic suliactanUalkyl methacrylate," 1999, Polymer, 40:3763-3772.
Chern, C.S., et al., "A competitive particle nucleation mechnism in the polymerization of homogenized styrene emulsions," 2003, European Polymer Journal, 39:1421-1429.
Erdem, B., et al., "Encapsulation of Inorganic Particles via Miniemulstion Polymerization. I. Dispersion of Titanium Dioxide Particles in Organic Media Using OLOA 370 as Stabilizer," 2000, J Polym Sci Part A: Polym Chem, 38:4419-4430.
Erdem, B., et al., "Encapsulation of Inorganic Particles via Miniemulstion Polymerization. II. Preparation and Chracterization of Styrene Miniemulsion Droplets Containing Ti02 Particles," 2000, J Polym Sci Part A: Polym Chem, 38:4431-4440.
Erdem, B., et al., "Encapsulation of Inorganic Particles via Miniemulstion Polymerization. III. Characterization of Encapsulation," 2000, J Polym Sci Part A: Polym Chem, 38:4441-4450.
Feng, J., et al., "Polymer Blend Latex Films: Morphology and Transparency," 1995, Macromolecules, 28:7671-7682.
Goodwin, J.W., et al., "The Preparation and Chracterisation of Polymer Latices Formed in the Absence of Surface Active Agents," 1973, Br Polym J, 5:347-362.
Goodwin, J.W., et al., "Studies on the Preparation and Characterisation of Monodisperse Polystyrene Latices III. Preparation Without Added Surface Active Agents," Colloid & Polymer Sci, 1974, 252, pp. 464.
Hantzchel, N., et al., "Poly(N-vinylcaprolactam-co-glycidyl methacrylate) Aqueous Microgels Labeled with Fluorescent LaF3:Eu Nanoparticles," 2007, Langmuir, 23:10793-10800.
Huhtinen et al., "Synthesis, Characterization, and Application of Eu(III), Tb(III), Sm(III), and Dy(III) Lanthanide Chelate Nanoparticle Labels," Anal. Chem., 2005.
Joumaa, N., et al., "Synthesis of Quantum Dot-Tagged Submicrometer Polystyrene Particles by Miniemulsion Polymerization," 2006, Langmuir, 22:1810-1816.
Kawaguchi, S., et al., "Surface Characterization and Dissocation Properties of Carboxylic Acid Core-Shell Latex Particle by Potentiometric and Conductometric Titration," 1995, J Colloid and Interface Sci, 176:362-369.
Kim, H-8., et al., "Synthesis, structure and film-forming properties of poly(butyl methacrylate)-poly(methacrylic acid) core-shell latex," 1994, Polymer 35/8: 1779-1786.
Kuang, M., et al., "Fabrication of Multicolor-Encoded Microspheres by Tagging Semiconductor Nanocrystals to Hydrogel Spheres," 2005, Adv Mater, 17/3, pp. 267-270.
Landfester, K., et al., "Evidence for the preservation of the particle identity in miniemulsion polymerization," 1999, Macromol Rapid Commun, 20/2:81-84.
Landfester, K., et al., "Formulation and Stability Mechanisms of Polymerizable Miniemulsions," 1999, Macromolecules, 32:5222-5228.
Landfester, K., et al., "Polyreactions in Miniemulsions," 2001, Macromol Rapid Commun, 22/12:896-936.
Lee, S., et al., "The Mechanism of Core-Shell Inversion in Two-Stage Latexes," 1992, J Polym Sci Part A: Poly Chem, 30:865-871.
Liu et al., "Method for Quantitative Proteomics Research by Using Metal Element Chelated Tags Coupled with Mass Spectrometry," Anal. Chem. 2006, v. 78, pp. 6614-6621.
Lortie, F., et al., "Structural and Rheological Study of a Bis-urea Based Reversible Polymer in an Apolar Solvent," 2002, Langmuir, 18:7218-7222.
Lou, X., et al., "Polymer-Based Elemental Tags for Sensitive Bioassays," 2007, Angew Chem. Int Ed, 46, pp. 6111-6114.
Matsuya, T., et al., "A Core-Shell-Type Fluorescent Nanosphere Possessing Reactive Poly(ethylene glycol) Tethered Chains on the Surface for Zeptomole Detection of Protein in Time-Resolved Fluoreometric Immunoassay," 2003, Analy Chem, 75:6124-6132.
Maxwell, I.A., et al., "Entry of Free Radicals into Latex Particles in Emulsion Polymerization," 1991, Macromolecules, 24:1629-1640.
Meguro, Y., et al., "Steric effect of B-diketone in synergistic extraction of actinide(III) and lanthanide( II I) with B-diketone+ 18-crown-6 ether/1,2-dichloroethane," 1998, J Alloys and Compounds, 271-273, 790-793.
Melby, L.R., et al., "Synthesis and Fluorescence of Some Trivalent Lanthanide Complexes," 1964, JAGS, 86:5117-5125.
Morin, M., et al., "Detection of Europium (III) and Samarium (III) by Chelation and Laser-Excited Time-Resolved Fluorimetry," 1989, Anal Chim Acta, 219:67-77.
O'Callaghan, K.J., et al., "Mixed Initiator Approach to the Surfactant-Free Semicontinuous Emulsion Polymerization of Large MMA/BA Particles," 1995, J Appl Polym Sci, 58:2047-2055.
Quinn, Z.A., et al., "Simultaneous Determination of Proteins Using an Element-Tagged Immunoassay Coupled with ICP-MS Detection," 2002, JAAS, 17:892-896.
Ramirez, L.P., et al., "Formation of Novel Layered Nanostructures from Lanthanide-Complexes by Secondary Interactions with Ligating Monomers in Miniemulsion Droplets," 2006, Macromolecular Chem and Phys, 207:160-165.
Sarkar, S., et al., "Thermal Decomposition of Potassium Persulfate in Aqueous Solution at 50-C in an Inert Atmospher of Nitrogen in the Presence of Acroylonitrile Monomer," 1988, J Appl Polym Sci, 35:1441-1458.
Schork, F.J., et al., "Miniemulsion Polymerization," 2005, Adv Palm Sci, 175:129-255.
Shigematsu, T., et al., "Determination of Manganese in Natural Waters by Atomic Absorption Spectrometry with a Carbon Tube Atomizer," 1969, Anal Chim Acta, 46:101-106.
Song, J-S., et al., "Monodisperse, micrometer-sized low molar mass polystyrene particles by two-stage dispersion polymerization," 2006, Polymer 47:4557-4563.
Soukka, T.,et al., "Utilization of Kinetically Enhanced Monovalent Binding Affinity by Immunoassays Based on Multivalent Nanoparticle-antibody Bioconjugates," Anal. Chem., 2001, v. 73, pp. 2254-2260.
Thomas et al.,"Nanosphere-antibody conjugates with releasable fluorescent probes", Fresenius J. Anal, Chem., 2001. v.369,pp. 477-482.
Vancaeyseele, C., et al., "Lanthanide-Containing Polymer Nanoparticles for Biological Tagging Applications: Nonspecific Endocytosis and Cell Adhesion," 2007, J Am Chem Soc, 129:13653-13660.
Verpoorte, E., "Beads and Chips: New Recipes for Analysis," 2003, Lab Chip, 3:60N-68N.
Xiao, M., et al., "Quantum Yields of Luminescnet Lanthanide Chelates and Far-Red Dyes Measured by Resonance Energy Transfer," 2001, J Am Chem, 123:7067-7073.
Yang, Y. et al., "Incorporating CdTe Nanocrystals into Polystyrene Microspheres: Towards Robust Fluorescent Beads," 2006, Small, 217:898-901.
Yildiz, U., et al., "The Frabrication of Very Small Miniemulsion Latexes from N-Stearoylglutamate and Lauryl Methoacrylate: Evidence for Droplet Budding," 2003, Macromol Chem Phys, 204:1966-1980.
Extended Search Report issued in EP 07844843.8, dated Jan. 3, 2011, 8 pages.
International Search Report issued in PCT/US07/83465, dated Jul. 31, 2008, 5 pages.
USPTO, Office Action from U.S. Appl. No. 12/332,812, dated Jan. 3, 2012, 21 pages.
USPTO, Office Action from U.S. Appl. No. 12/332,812 dated May 2, 2011, 40 pages.

* cited by examiner

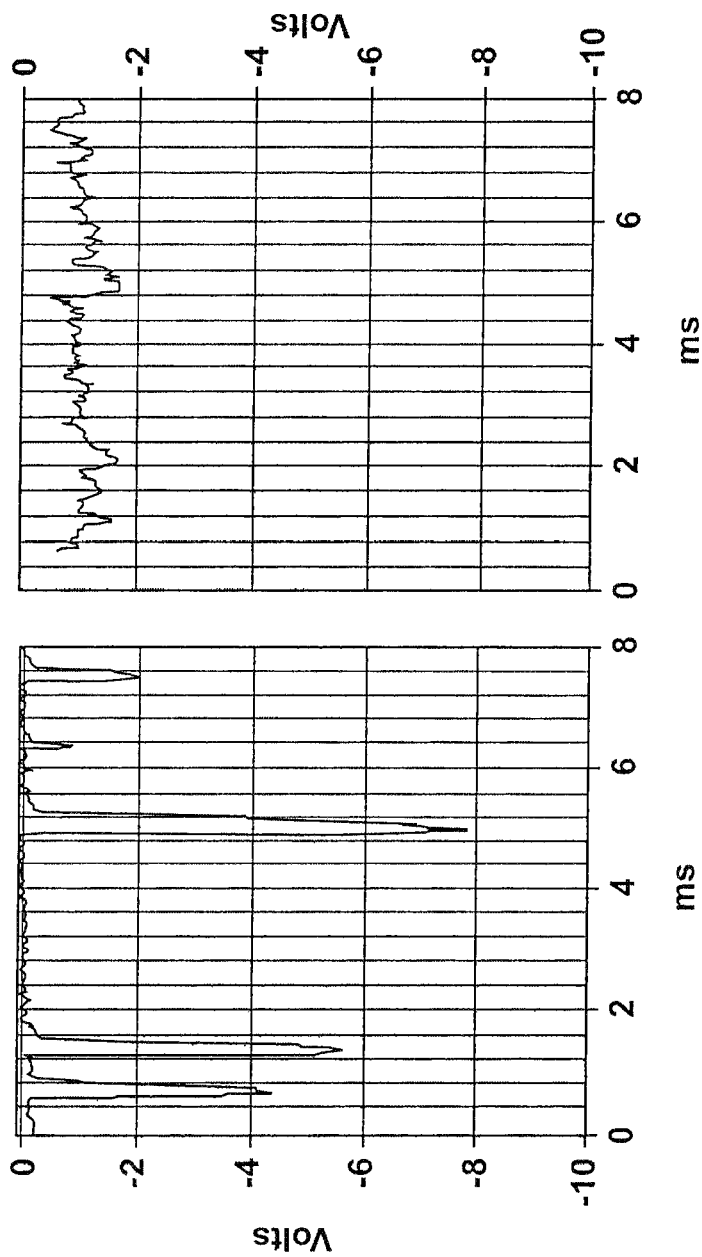

Elens 14v

Elens 9.5v
Opt. for Tb

MASS SPECTROMETRY BASED MULTI-PARAMETRIC PARTICLE ANALYZER

CROSS-REFERENCE TO RELATED APPLICATIONS

This application is a continuation of U.S. patent application Ser. No. 15/888,871, filed Feb. 5, 2018, which is a continuation of U.S. patent application Ser. No. 13/294,799, filed Nov. 11, 2011, which is a continuation of U.S. patent application Ser. No. 12/322,812, filed Dec. 11, 2008, which is a divisional of U.S. Pat. No. 7,479,630, issued Jan. 20, 2009, which is a non-provisional of U.S. Patent Application Ser. No. 60/555,952, filed Mar. 25, 2004, all of which are hereby incorporated by reference.

The entire contents of U.S. patent application Ser. No. 09/905,907, filed Jul. 17, 2001 and entitled Elemental Analysis of Tagged Biologically Active Materials (published as US 2002/0086441); and Ser. No. 10/614,115, filed Jul. 3, 2003 and entitled Elemental Analysis of Tagged Biologically Active Materials (published as US 2004/0072250) are hereby incorporated by reference.

The entire contents of U.S. Pat. No. 6,524,793, filed Jun. 18, 1999 and entitled Multiplexed Analysis of Clinical Specimens Apparatus and Method; International Patent Application Publication WO 98/33203, published Jul. 30, 1998, and entitled Gate For Eliminating Charged Particles in Time of Flight Spectrometers; and each of the publications cited in the Reference Section herein are hereby incorporated by reference.

FIELD OF THE INVENTION

The invention features apparatus and methods for sequentially analyzing particles, for example single cells or single beads, by spectrometry. In particular, the invention provides elemental-flow cytometers.

BACKGROUND OF THE INVENTION

The ability to analyze single particles, for example single cells or single beads, is a useful tool in the health sciences, in human and animal food sciences, in environmental sciences, forensic sciences, and in genomics and proteomics.

In the health sciences, cells are recognized as members of certain classes, for example normal cells or cancerous cells for diagnostic or biomedical research purposes. Cells carry multiple antigens or biomarkers [1], either extracellularly or intracellularly [2], which can be quantified or qualified for clinical medicine [3] or biomedical research [4] purposes. These methods are useful for development of pharmaceutical products particularly in the development of cell based assays and toxicity studies.

For example, chronic lymphocytic leukemia (CCL) is recognized as a unique disorder of B-cells [5, 6]. CCL is a disease with an uncertain clinical picture, and is often misdiagnosed resulting in inadequate treatment. However, a more detailed study of a patient's cellular immunophenotypic profile allows reclassification of the patient, which leads to a more personalized diagnosis and treatment. Such classification requires multi-targeted analysis of many markers on a cell membrane as well as in-cell antigens, their qualitative and quantitative description, and consideration of minute concentration variances.

Other examples in the health sciences include the analysis of single cells in the subclassification of non-Hodgkin's lymphoma. In addition, single cell analysis is useful in immunophenotyping of helper T-cells, and the determination of the ratio of CD4 to CD8 T-cells, for indication of the HIV progression in HIV positive patients. Further, the technique can be used to analyze single cells from patients with renal, cardiac and bone marrow transplants, for discriminating between graft rejections and viral infections in post-operative patients.

In human and animal food sciences, the analysis of single cells can be used to detect artificial hormones, pesticides, herbicides or antibiotics. Finally, in environmental sciences, the analysis of single cells can detect toxic waste, for example, in plant or bacterial cells.

A known method of analyzing single cells is by a fluorescence activated cell sorter (FACS). FACS is a technology to measure biological properties of cells by scanning single cells as they pass through a laser beam. Cells are usually stained with one or more fluorescent dyes specific to cell components of interest, for example, receptors on the cell surface and DNA of the cell nucleus, and the fluorescence of each cell is measured as it traverses the excitation beam. Since the amount of fluorescence emitted is proportional to the amount of fluorescent probe bound to the cell antigen, antibodies conjugated to fluorochromes are routinely used as reagents to measure the antigen both qualitatively and quantitatively on and in the cell. Primarily, researchers use the sorting function of the FACS machines to investigate cell receptors and other membrane antigens on a specific cell population. It can be used for antibody screening in multiple cell lines simultaneously (for example, a transfected cell line expressing the antigen of interest and a control cell line not expressing the antigen). In its simplified flow cytometry function, FACS machines are used mostly without sorting, which allows for example the use of fixed permeabilized cells and analysis of intracellular antigens. Many routine flow cytometry methods that identify antigens expressed on the cell surface and within the cell using specific antibodies, as well as general immunoassay methods for clinical diagnostics and treatment have been developed. Some of them involve multiplexing through the use of different fluorochromes and lasers. Deficiencies of this approach are related to limitations and difficulties of cell staining methods and spectral overlap of fluorochromes. Other measurable optical parameters include light absorption and light scattering, the latter being applicable to the measurement of cell size, shape, density, granularity, and stain uptake.

U.S. patent application Ser. No. 09/905,907, published under US 2002/0086441 on Jul. 4, 2002, and Ser. No. 10/614,115, describe labeling of analytes for analysis by mass spectrometry. Biologically active materials (for example, antibodies and aptamers) are labeled and conjugated to analytes prior to analysis.

SUMMARY OF THE INVENTION

In one broad aspect, the present invention provides an apparatus for introducing particles sequentially and analyzing the particles (for example, single particles such as single cells or single beads), by spectrometry. The apparatus, an elemental flow cytometer, is an instrument comprising: a means for introducing single particles sequentially, a means to vaporize, atomize, and excite or ionize the particles or an elemental tag associated with an analyte on the particles, and a means to analyze the elemental composition of the vaporized, atomized, ionized and/or excited particles, or an elemental tag associated with the particles.

It is to be understood that although the term "means for introducing single particles sequentially" is used, this may encompass introduction of a predetermined number of particles (for example, 2 or more) in discrete 'packets'.

It is also to be understood that the term "means to vaporize, atomize, and excite or ionize" includes means where atomization may not be necessary, so that the term may or may not encompass vaporization followed by ionization directly. In some applications, such as for example optical emission spectrometry (OES), it is not essential to ionize the sample; emission from atomic species can be sufficient. For OES, it is necessary only to excite the atoms (or ions) to cause emission. Thus, for example, "vaporize, atomize and ionize" should be understood to mean vaporize, atomize and ionize (for mass spectrometry) or excite (either or both atoms and ions) for OES.

Another aspect of the invention is an analytical instrument. The instrument has a sample introduction system for generating a stream of particles from a sample. An ionization system receives particles in the stream. The ionization system is operable to atomize particles in the stream as the particles are received from the sample introduction system and to ionize atoms from the atomized particles. The instrument has an ion pretreatment system and a mass analyzer. The ion pretreatment system is adapted to transport ions generated by the ionization system to the mass analyzer. The mass analyzer is adapted measure the amount of at least one element in individual particles from the stream by performing mass analysis on the ions from the atomized particles.

Another aspect of the invention is an instrument for performing multi-parametric quantitative analysis of particles in a stream of particles. The instrument has a sample introduction system for generating a stream of particles from a sample. A particle analyzer is adapted to measure the amount of each of a plurality of at least five different tags in each of a plurality of particles in the stream of particles produced by the sample introduction system. The particle analyzer has a detector adapted to generate signals corresponding to each tag. The signals generated by the detector corresponding to each of the tags is independent from the signal generated by the detector corresponding to the others of the tags.

In another broad aspect, the invention provides a method for analyzing particles that have been introduced sequentially, such as single cells or single beads, by spectrometry. A trigger will report the ion cloud arrival with following analysis, including for example initiation of data acquisition. Triggering may be based, for example on light scattering or on an ion current change or ion composition change.

Another aspect of the invention is an elemental flow cytometer, comprising: a means for introducing particles sequentially into a device to vaporize, atomize and excite or ionize the particles, or an elemental tag associated with the particles; a device to vaporize, atomize and excite or ionize the particles, or an elemental tag associated with the particles, downstream of the means for introducing particles sequentially; and a spectrometer to analyze the vaporized, atomized and ionized and/or excited particles, or the elemental tag associated with the particles.

Another aspect of the invention is a mass-spectrometer-based flow cytometer, comprising: a means for introducing particles sequentially into a device to vaporize, atomize and ionize the particles, or an elemental tag associated with the particles; a device to vaporize, atomize and ionize the particles, or an elemental tag associated with the particles, downstream of the means for introducing particles, sequentially; and a mass spectrometer operatively connected and downstream of the device to vaporize, atomize and ionize.

Another aspect of the invention is a mass-spectrometer-based flow cytometer, comprising: a means for introducing particles sequentially into a device to vaporize, atomize and ionize the particles, or an elemental tag associated with the particles; a device to vaporize, atomize and ionize the particles, or an elemental tag associated with the particles, downstream of the means for introducing particles sequentially; an ion pretreatment device operatively connected and downstream of the device to vaporize, atomize and ionize; and a mass spectrometer operatively connected and downstream of the ion pretreatment device. The ion pretreatment device may be provided as a part of the mass spectrometer, preferably upstream of the mass analyzer section thereof.

Another aspect of the invention, is an optical emission spectrometer-based flow cytometer, comprising: a means for introducing particles sequentially into a device to vaporize, atomize and excite or ionize the particles, or an elemental tag associated with the particles; a device to vaporize, atomize and excite or ionize the particles, or an elemental tag associated with the particles downstream of the means for introducing particles sequentially, and an optical emission spectrometer to analyze the vaporized, atomized and excited or ionized particles, or the elemental tag associated with the particles downstream of the device to vaporize, atomize and excite or ionize the particles.

Another aspect of the invention, is a method of analyzing particles that have been introduced sequentially into a device to vaporize, atomize and excite or ionize, comprising: sequentially introducing particles or particles associated with an elemental tag, into a device to vaporize, atomize and excite or ionize the particles or the elemental tag associated with the particles; and introducing the vaporized, atomized and excited or ionized particles, or the elemental tag associated with the particles into a spectrometer.

The labeling or tagging of the single particles with elemental tags can be done, for example, using the methods and system disclosed in U.S. Ser. No. 09/905,907 and U.S. Ser. No. 10/614,115, both applications of which are herein incorporated by reference. U.S. Ser. No. 09/905,907 and U.S. Ser. No. 10/614,115 describe methods and systems for the analysis of biologically active materials conjugated to analytes by mass spectrometry. Other methods of labeling or tagging the particles will also serve. If, for example, the particles are beads, the particles themselves can be labeled either on the surface or within their bodies, as disclosed herein.

Another aspect of the present invention is to provide kits having reagents for carrying out the methods of the present invention and instructions for these methods.

Another aspect of the present invention is to provide beads with an affinity substance as a carrier to measure an analyte in a sample, further comprising an elemental label or tag. The elemental tag can be on the analyte, on the affinity substance or (and) on or in the bead itself.

BRIEF DESCRIPTION OF THE DRAWINGS

FIG. 11A shows an analog signal from an oscilloscope registered while continuously monitoring $Na^+$. in a cell suspension in a 30 mM $CaCl_2$ buffer.

FIG. 11B shows an analog signal from an oscilloscope registered while continuously monitoring $Na^+$. for a 30 mM $CaCl_2$ buffer.

DEFINITIONS

Figure 1:
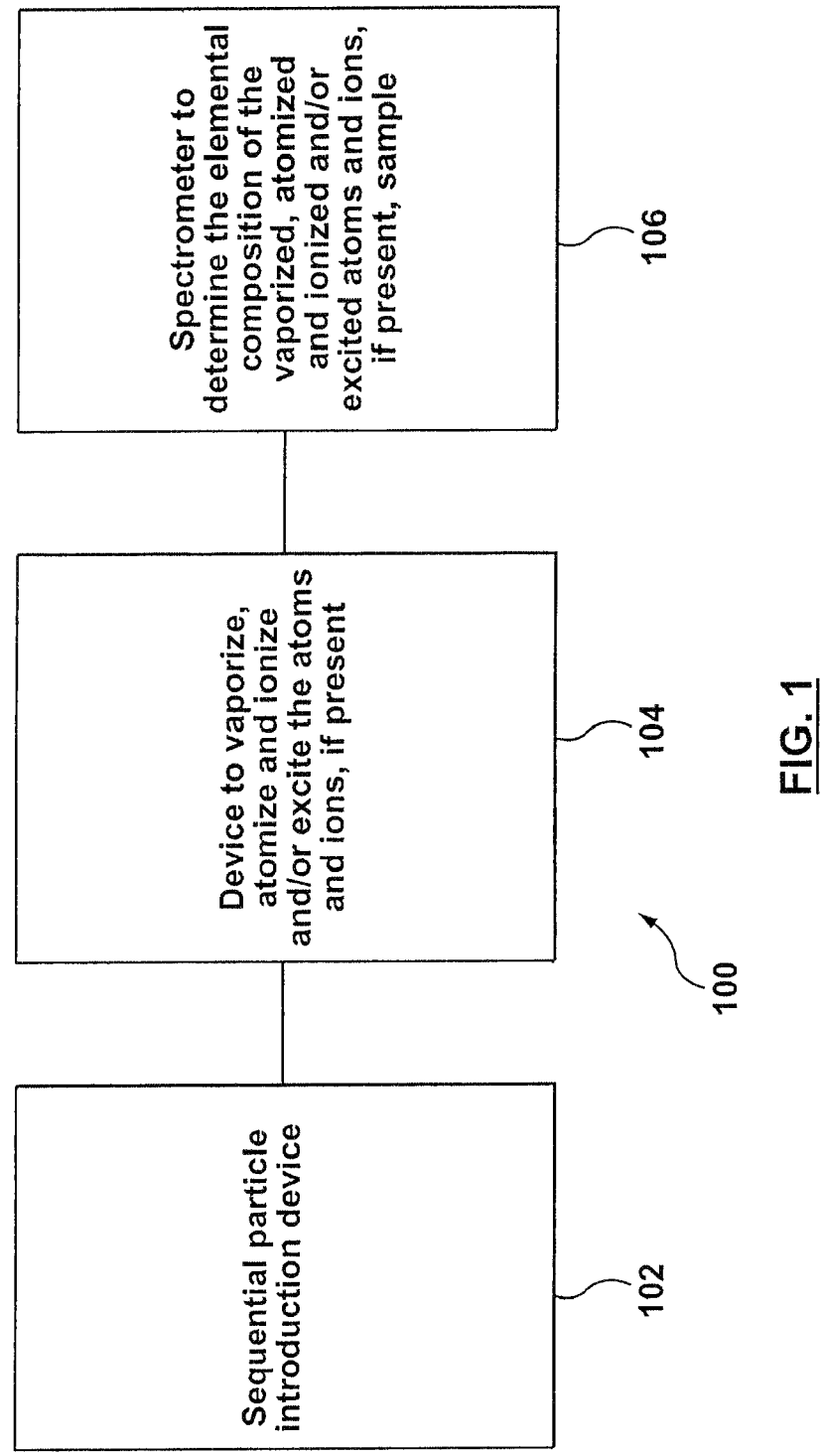
FIG. 1 is a schematic diagram of a flow cytometer according to the invention.

ICP-MS: is an Inductively-Coupled Plasma Mass Spectrometer.

FACS: is a Fluorescence Activated Cell Sorter.

Various aspects of the present disclosure are described herein with reference to single particles. However, in some cases, these aspects of the present disclosure can be used with packets of a predetermined number of discrete entities (e.g., 2, 3, or 4). Various aspects of the present disclosure as described herein can be used with single cells, single beads, single bacteria, single viral particles, single pollen particles, single microscopic insects such as dust mites.

Tag (or label): a chemical moiety that provides a distinguishable signal of the presence of the analyte or analyte complex with which it is associated, as for example through linkage to an affinity product that in turn recognizes the analyte or analyte complex. As disclosed herein, the tag (which is also called an "elemental tag") can contain an element or an isotope (or multiple copies thereof) that provide the distinguishable signal. A tag can include for example an element or isotope of an element that is associated with an analyte or analyte complex and which is measured to determine the presence of the analyte. A tag can also include, for example, any distinguishable component (e.g., an element or isotope or multiple copies thereof) that is provided on the surface or within the body of, or is otherwise associated with, a particle and serves to distinguish that particle from other particles.

TOF-MS: is a Time-of-Flight Mass Spectrometer

DESCRIPTION OF SPECIFIC EMBODIMENTS INCLUDING THE BEST MODE CURRENTLY CONTEMPLATED BY THE INVENTORS

The elemental flow cytometer of the present invention provides for the identification and quantitative analysis of particles that have been introduced sequentially into a device to vaporize, atomize and excite or ionize them, for example individual cells or microscopic beads, by measuring the elemental composition of the single particle (or any distinctive part of cell or bead), or a tag or label associated with an analyte located on or in the cell or bead by employing the mass-to-charge ratio or optical emission of the disintegrated tag elements. The tag can be of any chemical nature, as it is only its elemental composition that is important. In comparison, the chemical structure of the appropriate tag is absolutely critical to provide a unique fluorescence in FACS.

The elemental flow cytometer includes:
means for introducing particles sequentially (for example, cell-by-cell or bead-by-bead), preferably adapted for discrete event analysis;
means to vaporize, atomize and excite or ionize the particles,
or an elemental tag (or classifiable elemental composition) associated with an analyte of interest on or in the particles to quantify the analyte of interest associated with the particles;
and means for registering the information on elemental composition of the particles, or an elemental tag associated with an analyte on the particles. This can be done, for example, by mass spectrometry (MS) or by optical emission spectrometry (OES).

Elemental flow cytometers according to the invention are quantitative analytical instruments [7]. They can perform the task of quantitative or qualitative analysis of biological or environmental samples using analytical methods [8].

Beads with an affinity substance can be used as carriers to measure an analyte in a sample. The placement of the elemental tag or label can be on the analyte, on the affinity substrate, and/or on or in the bead itself.

Specific embodiments of the elemental flow cytometer include: (1) a mass spectrometer based flow cytometer (MS FC) and (2) an optical emission spectrometer based flow cytometer (OES FC).

A mass spectrometer based flow cytometer (MS FC) comprises:
means for introducing particles sequentially:
means to vaporize, atomize and ionize the particles and/or any tags that may be associated with the particles; and
a mass spectrometer to analyze the elemental composition of the vaporized, atomized and ionized particles, and/or any tags that may be associated with the particles.

MS FCs according to the invention can further comprise ion pretreatment devices, for pretreatment of ions prior to analysis by the mass spectrometer.

The means to vaporize, atomize and ionize the single particles may include glow discharge, graphite furnace, and capacitively coupled plasma devices, or other suitable devices. Preferably, the means to vaporize, atomize and ionize the single particle includes an inductively coupled plasma (ICP) device because it has a capacity to disintegrate, vaporize, atomize and ionize cells and beads during their short residence time in the plasma and because the ICP is particularly tolerant of concomitant materials, is robust to changes of the composition of the plasma gases, and is a highly efficient atomizer and ionizer.

The ion pretreatment device acts, inter alia, as an interface between atmospheric conditions in the vaporizer/atomizer/ionizer and the vacuum in the mass spectrometer. In addition, the very strong ion current originating from this source is dominated by space charge, which could be reduced by an accelerating potential and/or by rejection of major plasma ions on the basis of their mass-to-charge ratio ($Ar^+$, for example). In the case of a TOF MS, the ion pretreatment device also conditions the ion flow for the needs of the TOF mass analyzer. For example, it will narrow the ion energy distribution and focus the parallel ion beam close to the axis of the mass analyzer.

The mass spectrometer can be any mass spectrometer. For example, it can be a quadrupole, magnetic sector with array detector, 3D Ion Trap or Linear Ion Trap mass spectrometer. Preferably it is a time of flight mass spectrometer (TOF MS). TOF MS is a simultaneous analyzer. It is able to register all masses of interest in one particle simultaneously.

The optical emission spectrometer based flow cytometer (OES FC) comprises:

a means for introducing particles sequentially; a means to vaporize, atomize and excite or ionize the particles, and/or any tags that may be associated with the particles; and an optical emission spectrometer to analyze the elemental composition of the vaporized/atomized and excited or ionized particles and/or any tags that may be associated with the particles.

The means to vaporize, atomize and excite or ionize the single particles may include glow discharge, graphite furnace, and capacitively coupled plasma devices, or other suitable devices. Preferably, the means to atomize and ionize the single particles includes an inductively coupled plasma (ICP) device because it has a capacity to disintegrate, atomize and excite or ionize cells and beads during their short residence time in the plasma and because the ICP is particularly tolerant of concomitant materials, is robust to changes of the composition of the plasma gases, and is a highly efficient atomizer and ionizer.

Processes implemented by elemental flow cytometers according to the invention can also include an in-line lysis step between the means for single particle introduction and the means to vaporize, atomize and ionize.

The embodiments will now be described in detail.

In a most general aspect, the present invention provides an elemental analyzer as a detector for a flow cytometer. FIG. 1 shows schematically a cytometer 100 suitable for use implementing methods of analysis according to the invention. Cytometer 100 comprises means 102 for introducing particles sequentially, for example a cell or particle injector 171 (FIGS. 2, 3, 4), operatively connected upstream of a device 104 for vaporizing, atomizing and exciting or ionizing particles or elemental tags associated with the particles. The elemental composition of the particle or elemental tag is determined by a spectrometer 106 operatively connected to the device 104. Spectrometer 106 may, for example, include an optical spectrometer 157, which detects the emission from excited atoms and/or ions, or a mass spectrometer 116 which detects the ions.

In one embodiment the present invention provides a mass-spectrometer based flow cytometer (MS FC) 101. A schematic representation of such an embodiment is given in FIG. 2.

Figure 2:
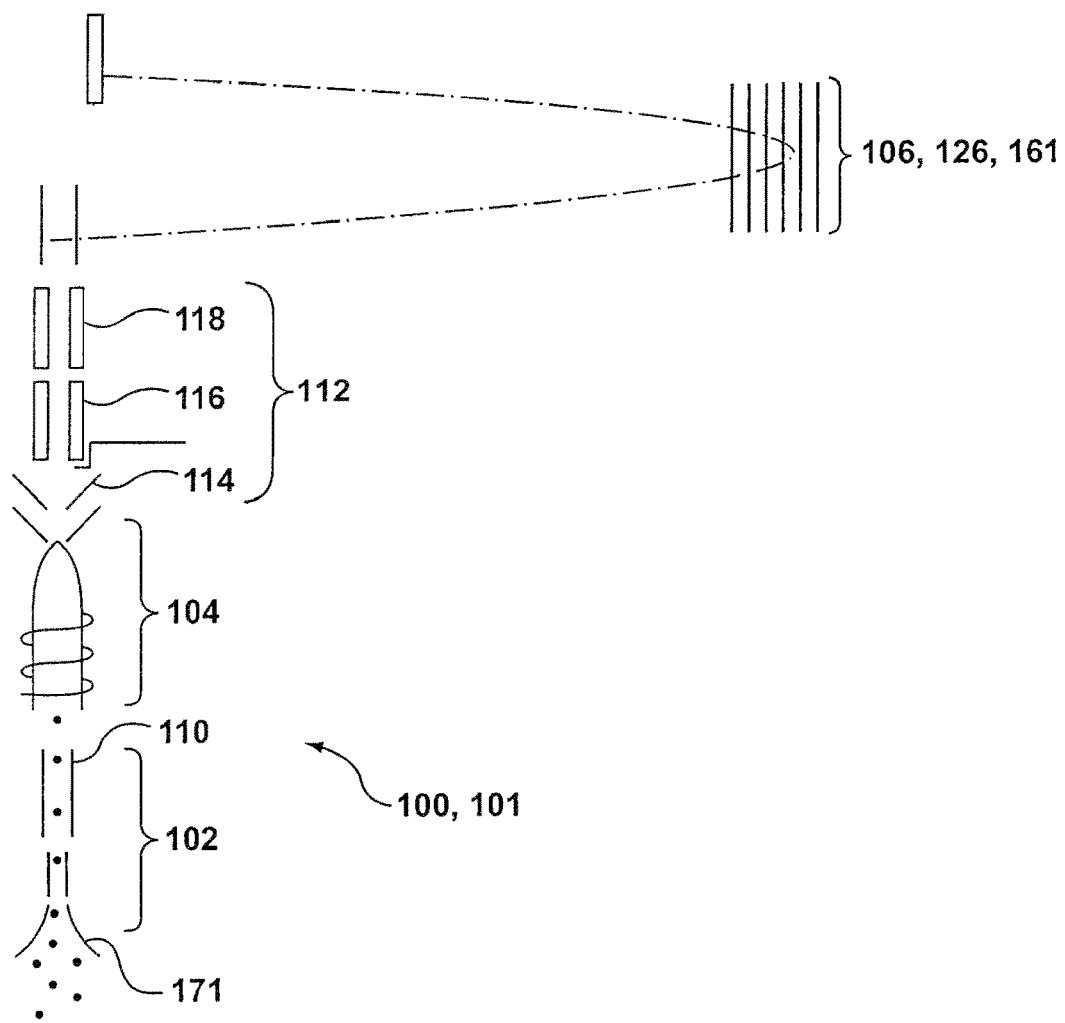
FIG. 2 is a schematic diagram of an embodiment of a mass-spectrometer-based flow cytometer according to the invention.

Referring to FIG. 2, mass-spectrometer based embodiment 101 of cytometer 100 comprises means 102 for introducing particles sequentially, for example a cell or particle injector 171, operatively connected upstream of device 104 for vaporizing, atomizing and exciting or ionizing particles or elemental tags associated with the particles, namely an inductively coupled plasma (ICP) vaporizer/atomizer/ionizer. In the embodiment shown, means 102 comprises optional in-line lysis system 110.

Ion pretreatment device 112, in this instance comprising vacuum interface 114, high-pass filter 116 and gas-filled "cooler" cell 118, is operatively connected downstream of the ICP vaporizer/ionizer.

Time-of-flight (TOF) mass spectrometer 106, 161, 126 is operatively connected downstream of the ion pretreatment device. Use of mass spectrometer-based cytometer 101 according to such embodiments to analyze single particles can provide greatly improved accuracy, large dynamic range and high sensitivity, compared to prior art systems. In addition, because a large number of distinguishable elements and isotopes can be used as tags, and because the mass spectrometer provides high abundance sensitivity (exceedingly small overlap of signal on adjacent mass/charge detection channels), it facilitates a higher order of multiplexing (simultaneous determination of multiple analytes, each distinguishably tagged) than prior art fluorescence-based detection flow cytometers. Further, because of the high resolution of adjacent mass/charge detection channels and the large linear dynamic range of the mass spectrometer, the instrument provides for a large dynamic range both for a given analyte and between analytes. Thus, in many instances generic tagging moieties can be used in analyses in which the copy-count of the analytes differs dramatically; this distinguishes the method from conventional fluorescence detection methods for which the composition of the several fluorophores used for multiplex assay must often be adjusted for a particular assay to provide emission intensities of similar magnitude to minimize spectral overlap. Thus such embodiments can provide researchers and clinicians substantially improved analytical and prognostic capabilities.

Another important application of cytometers according to this embodiment of the invention is to multiplex assay distinguishable beads, where the beads are distinguished by their elemental compositions and have attached affinity products that recognize an antigen in the sample into which they are introduced, where the antigen is then further recognized using a sandwich (or other) assay employing yet a further distinguishable element.

Significant components of the mass spectrometer-based flow cytometer 101 of FIG. 2 and methods of use will now be described in detail.

Tagging

In Certain Cases the Particle (For Example a Single Cell) Will Not Require Tagging In some cases a particles will not require tagging. For example, if a single cell contains or is bound to an element that is detectable against the background by mass spectrometry, no tagging is required. For example, for the analyses of bacterial or plant cells that accumulate elemental species in bioremediation, additional tagging would not be required. Further, the intracellular accumulation of metal, for example platinum- or gold-containing drugs would not require additional tagging.

In Cases Where Single Particles Require Tagging

Tagging of particles can be done by many methods as is known to those of skill in the art. For example, fluorescent dyes which have a succinimidyl ester moiety react efficiently with primary amines of proteins (antibodies) to form stable dye-protein conjugates. In a first step to tag DNA, an amine-modified nucleotide, 5-(3-aminoallyl)-dUTP, can be incorporated into DNA using conventional enzymatic tagging methods. In a second step, the amine-modified DNA can be chemically tagged using an amine-reactive fluorescent dye. Biotinilation of antibodies can be carried out using sulfhydryl-directed solid-phase chemistry. These methods are well established and are available in kit formats from different companies, including for example Molecular Probes Inc, Pierce Chemical Company, and others. Specific chemical reactions are known in radioimmunochemistry. For example, radionuclides (88/90)Y and (177)Lu can be used to tag antibodies using cyclic diethylenetriaminepentaacetic acid anhydride (cDTPA), isothiocyanatobenzyl-DTPA (SCN-Bz-DTPA), or 1,4,7,10-tetraazacyclododecanetetraacetic acid (DOTA)(PMID: 14960657).

Elemental analysis of tagged biologically active materials has been disclosed in the incorporated references, U.S. patent application Ser. Nos. 09/905,907 and 10/614,115. Tagged biologically active materials, for example, antibodies and aptamers, etc., that react specifically with cellular components can be used to tag cells. Other affinity products are known to those skilled in the art. For example, they may include antigens, RNA, DNA, lipoproteins, glycoproteins, peptides, polypeptides, hormones, etc.

Although in many applications of systems and methods according to the invention it is convenient to tag each biologically active material (for example an antibody, aptamer or antigen) with a single element or isotope, it should be readily appreciated by those skilled in the art that an antibody or antigen may be tagged with more than one element. As there are more than 80 naturally-occurring elements having more than 250 stable isotopes, there are numerous elements, isotopes, and combinations thereof to choose from. Within limits prescribed by the need to have distinguishable tags when in combination, this will allow for simultaneous detection of numerous biologically-tagged complexes. It is advantageous if the relative abundance of the tag elements is sufficiently different from the relative abundance of elements in a given sample under analysis. By "sufficiently different" it is meant that under the methods of the present invention it is possible to detect the target antibody or antigen over the background elements contained in a sample under analysis. Indeed, the difference in inter-elemental ratios of the tagged antibody or antigen, and the sample matrix can be used advantageously to analyze the sample.

It is feasible to select elemental tags, which do not produce interfering signals during analysis. Therefore, two or more analytical determinations can be performed simultaneously in one sample. Moreover, because the elemental tag can be made containing many atoms, the measured signal can be greatly amplified.

The use of multiple copies of the element or isotope per tag can improve the sensitivity linearly, particularly, for example in the employment of ICP-MS embodiments of the invention. For multiplex assay of up to 23 simultaneous analytes, the tags can be conveniently constructed using the natural isotopic distributions of, for example, Ru, Rh, Pd, Ag, In, La, Ce, Pr, Nd, Sm, Eu, Th, Dy, Ho, Er, Tm, Yb, Lu, Hf, Re, Ir, Pt and Au. These elements, which are expected in most instances to be uncommon in biological samples, each have at least one isotope with natural abundance greater than 10% that is not significantly interfered by the others or by the oxide or hydroxide ions of the others. For those isotopes of lower natural abundance (e.g., $^{143}$Nd, 12.2%), tagging with the isotopically enriched isotope provides an obvious sensitivity advantage. Where a higher order of multiplexing is desired, the use of commercially-available enriched isotopes (of which there may be as many as 167 of 55 elements that are not expected to be common in biological systems) offers a possibility (depending, of course, on availability, cost and isotopic purity). For example, there are as mentioned at least 35 isotopes of the lanthanides and noble metals alone that may be obtained in enriched form, are note expected to be common in biological systems and are largely independent with respect to mutual interference (though some care in the selection of the tagging protocol is to be taken where large differences in copy counts of the analytes occur; for example, if the copy count of an analyte tagged with .$^{169}$Tm is 1000 times greater than for an analyte tagged with .$^{185}$Er, .$^{169}$TmO$^+$ will interfere significantly with the determination of .$^{185}$Er$^+$ since TmO$^+$ is typically about 0.07% of the Tm$^+$ signal (though, as for FACS, some of this interference can be corrected mathematically since the fractional formation of oxide ions is stable and can be calibrated). In special circumstances, it might be feasible to tag a given biologically active material with more than one element or isotope (for example, there are in theory 20 distinguishable 3-isotope tags that can be constructed from 4 isotopes).

The invention allows the development of a novel powerful technique to measure biological properties of cells by analyzing single cells as they pass through an ICP. When using antibodies as the affinity product (biologically active material) the amount of a tag element detected by the mass spectrometer is proportional to the amount of tagged affinity product bound to the cell. Antibodies conjugated to the elemental tag are routinely used as reagents to measure the antigen both qualitatively and quantitatively, for example acquiring the patient's immunophenotypic profile, which is almost unlimited in the number of markers of interest. Another advantage offered by the invention is a reduced need to enhance the antibody signal by "sandwich" immunostaining" which can result in analytical errors.

Methods according to the invention are distinct from the approach of conventional methods (such as fluorescence, radioimmunoassay, chemiluminescent assay) that are challenged by overlap of detector signals, limited dynamic range, time-sensitive signals, and in some instances sensitivity. Accordingly, the method offers the potential for massively multiplexed assay (limited principally by the independence and cross-reactivity of the affinity chemistry) with essentially no signal overlap. Where the elemental (isotopic) tags are quantitatively associated with specific affinity products, the quantitative characteristic of ICP-MS offers a novel opportunity for absolute determination of multiple antigens simultaneously.

The method and apparatus can, for example, detect as few as 100 copies of each tag per cell. It is estimated that for the detection of as few as 100 copies of each tag per cell, at least 70 atoms per tag will be required.

The invention provides the feasibility to perform massively multiplexed bead assays. Current fluorescence-based flow cytometers are frequently used for bead assays. In this application, beads are typically labeled with 2 fluorochromes in varying ratios, typically providing up to about 100 distinguishable beads as determined by the fluorophore emission ratio (see, for example, the incorporated reference, U.S. Pat. No. 6,524,793 and references therein). Each bead also has attached affinity products (e.g., antibodies) that recognize an analyte in a solution in which the bead is placed, each bead of different "colour" having an affinity product for a different analyte. Once exposed to the sample solution, the captured analyte is then sandwiched with another antibody having a third fluorophore reporter. Thus, in the flow cytometric analysis, the beads can be mixed, the copy-count of the analyte captured determined by the emission of the third fluorophore and the identity of the analyte determined by the ratio of the emissions of the bead-labeling fluorophores. Accordingly, the conventional fluorescence detector flow cytometer can perform multiplexed bead assays to as high 100 order (the number of distinguishable "colours", though in practice much fewer are used (presumably because of signal overlap, which limits the measurement accuracy (and thus confidence in the identification of the bead) when the ratio of the fluorescence emission intensity is large (e.g., one or two orders of magnitude, depending on the emission wavelength distributions).

A similar method can be implemented using mass spectrometer-based flow cytometers according to the invention, with the advantage that the degree of multiplexing can be vastly increased and the overlap of signals can be virtually eliminated from concern. For example, the bead can incorporate (either on its surface or, probably more conveniently, within its body, mixtures of elements or isotopes that can be used to report the identity of the bead. Assuming that the detector has a dynamic range of 3 orders of magnitude and that factors of 3 in relative signal can be reliably determined, 2 elements incorporated into the bead allows 63 distinguishable beads. Under the same assumptions but using 5 element labels provides 32,767 distinguishable beads, and if the dynamic range is 5 orders of magnitude, the same 5-element labels provide for 248,831 distinguishable beads. Furthermore, these few labeling elements can be selected so that signal overlap is nonexistent (e.g., by choosing them such that they appear at mass differences greater than a few atomic mass units), which enables the large dynamic range of detection. The sandwich assay for the analyte captured by the bead employs a yet different element tag, which also is readily distinguished from the bead-labeling elements. Further, in this configuration each bead can contain several affinity products to attach several different analytes per bead, each recognized by a sandwich assay using a yet different element, providing for multiplex assay both between beads and on a single bead. One anticipated application is for a 96-well plate (or 384-well, or 1536-well) for which a differently-labeled bead is provided to each well, and multiplexed element-tagged immunoassay on the bead surface in each well is conducted. The entire contents of the plate (96, or 384 or 1536 wells) can then be pooled and the result analyzed by flow cytometry, thus providing a type of mass spectrometer "plate reader" (where the bead identity, as determined by its elemental composition, identifies the well in which the assay took place).

Means for Introducing Particles Sequentially

The sample introduction system 102 can comprise several devices that are currently in use with other flow cytometry sample introduction systems. For example, there currently exist several cell or particle injector 171 systems in use for flow cytometry, including various formats of sheath flow injection. Because of considerations for solvent loading of the ICP (typically optimum for 25 to 80 µL/min), the "flow in air" (or in the instance of the ICP, "flow in argon") injector 171 may in some circumstances be considered most appropriate (though some improvement over current designs may be preferred, in order to minimize cell agglomeration). All sample introduction devices suitable for the purposes disclosed herein; including ICP devices, will serve, regardless of whether they now exist or are hereafter developed or improved.

For the feasibility experiments that we report below, a small volume spray chamber (similar in concept to a design reported by J. L Todoli and J. M Mermet, J. Anal. At. Spectrometry 2002, V17, 345-351) was employed, having a drain to remove condensed liquid (of which there was essentially none at the suspension flow rates used) and having no gas outlet except into the ICP.

It is noted that, compared to the FACS method for which careful alignment of the particles with the excitation laser is important, the present method allows relaxation of the alignment of the particles with the vaporizer, atomizer and ionizer (unless light scattering is used as the particle detection trigger; see later). This is because, especially for the ICP instance, the precise position of the particle within the injector tube feeding the ICP is of little importance to the detected signal (in part because the central channel flow containing the particle expands dramatically upon heating and in part because virtually all of the central channel flow is inhaled into the sampler of the ICP-MS vacuum interface, though only the predominantly central portion is subsequently transmitted through the skimmer; in any event, there appears to be substantial mixing of the central channel flow prior to sampling into the vacuum interface).

It is desirable that the entire particle introduced to the ICP be vaporized, and at least partially atomized and ionized, so as to enable determination of the element tags contained within the particle (intracellular tags, or bead labels). Current wisdom holds that solid particles (e.g., of glasses or geological materials) smaller than about 1 µm diameter, and liquid aerosols smaller than about 10 µm diameter, are efficiently vaporized, atomized and ionized in the ICP, while larger particles may be only partially volatilized. This is presumably due to the short transit time of the particle through the ICP, for which the heat transfer to a large particle is insufficient to allow complete vaporization, atomization and ionization. Thus, it is propitious to use beads having a diameter smaller than about 1 µm diameter (for example, we used stober silica particles of about 150 nm diameter in our feasibility studies described below). However, cells are frequently larger than 10 µm diameter. Nonetheless, our feasibility experiments, described below, suggest that cells larger than this perceived minimum are, in fact, efficiently vaporized, atomized and ionized, from which we infer that, upon the rapid heating during transit through the ICP, the cell explodes into fragments that are small enough to be vaporized, atomized and ionized. It remains possible that in certain instances the particles may be too large to allow efficient vaporization, atomization and ionization, which could be indicated by the failure to observe an intracellular tag or the element labels of a bead. In this instance, several ion source parameters (gas flow, power, sampling depth) can be adjusted to alleviate this deficiency. Alternatively, an in-line lysis component can be employed.

In-line Lysis

In-line lysis system 110 may be advantageously employed in some circumstances. For example, in the event that whole cell introduction is not viable, use of an in-line lysis system can be advantageous. This may be done by any method suitable for the purposes disclosed herein, including a number of methods now known to persons skilled in the art, including acidification of the sheath flow fluid to cause cell collapse or high purity (low conductivity) water sheath flow to induce rupture of the cell by osmotic pressure. In this instance, the elemental tags will be retained and transmitted to the device to vaporize, atomize and ionize the sample, though the transient pulse may be broadened slightly by diffusion in the flow stream.

Means for Vaporizing/Atomizing/Ionizing

Any means 104 suitable for the purposes disclosed herein can be employed to vaporize, atomize and excite or ionize the particle or the elemental tag associated with the particle; for example, graphite furnace, glow discharge and capacitively coupled plasma. Preferably, the vaporizer/atomizer/ionizer is an inductively coupled plasma. In some instances, vaporization, atomization and ionization and/or excitation can occur in different devices and at different times (e.g., within a graphite furnace for vaporization in combination with ICP for atomization and ionization and/or excitation.

Inductively Coupled Plasma Mass Spectrometry (ICP-MS) is a preferred means of determining the elemental composition, especially ultra-trace components, of materials. It has found acceptance in various applications including environmental (e.g., drinking, river, sea and waste water analyses), geological (e.g., trace element patterning), clinical (e.g., determination of trace metals in blood, serum and urine) and high purity materials (e.g., semiconductor reagents and components) analysis.

ICP-MS couples an inductively coupled plasma ionization source to a mass spectrometer. Briefly, a sample, most commonly an aerosol produced by nebulization, is injected into a high temperature atmospheric pressure plasma obtained by the coupling of radio frequency (rf) energy into the flowing argon gas stream. The resultant plasma is characterized by a high temperature (ca. 5000K) and relatively high concentration (ca. 1015 cm.$^{-3}$) of equal numbers of electrons and positive ions. Provided that the particles of the nebulized sample are small enough, as described above, the sample is promptly vaporized, atomized and ionized as it flows through the plasma. The efficiency of ionization is inversely and exponentially dependent on the ionization potential of the elements, with the majority of the periodic table being nearly 100% ionized. The resultant plasma containing the ionized sample components is extracted into vacuum where the ions are separated from neutral species and subjected to mass analysis. The "mass fingerprint" identifies the elements contained in the sample. The detected signal is directly and quantitatively proportional to the concentration of the elemental composition of the sample. The particular attributes of the method of note include: wide linear dynamic range (9 orders of magnitude), exceptional sensitivity (sub-part per trillion, or attomole/microliter, detection), high abundance sensitivity ($<10^{-6}$ overlap between adjacent isotopes for quadrupole analyzers), counting-statistics-limited precision, absolute quantification, and tolerance of concomitant matrix.

ICP-OES is another preferred method of performing the analyses described above; it is of particular merit when the solids content of the sample is greater than about 1% (for homogeneous liquid introduction rate of the order of 1 mL/minute). The conditions employed in the ICP are comparable to those described for the ICP-MS method. Detection of the emission from excited neutral atoms and ions in the ICP provides for the quantitative determination of the elemental composition of the sample. Most current ICP-OES instruments provide array detection for true simultaneous determination across most of the periodic table. In many favorable instances, ICP-OES retains some of the desirable characteristics of ICP-MS, including wide dynamic range and well-resolved detection channels. In other instances, there is potential for inter-element or molecular emission interference, though in such instances alternate emission wavelengths are frequently available. The principal deficiencies for the application considered here are its generally lower sensitivity (in some instances limited by background emission signals) and its inability to distinguish isotopes of a given element. Nonetheless, ICP-OES is perceived to be more simple to use, more robust, and less expensive than ICP-MS, and hence may have application for the present method.

Ion Pretreatment Device

In some circumstances, as for example in MS FC, an ion-pretreatment device 112 may be used to condition the ions for the mass analyzer. Because the mass spectrometer operates at reduced pressure (typically less than $10^{-4}$ torr) and the ion sources noted above typically operate at higher pressure (e.g., atmospheric pressure for the conventional ICP), one function of the ion-pretreatment device is to efficiently transport the ions derived from the sample through a pressure reduction step (the vacuum interface). It is desirable in this step, and subsequently, to increase the ratio of ions to neutrals that are subsequently transmitted to the mass analyzer. Ion optical components (ion lenses) typically serve this function, by localizing the ions and allowing the neutrals to be removed through vacuum pumps. An additional function of the ion optics is to condition the ion beam (in space and energy) to match the acceptance of the mass analyzer.

High-pass filter 116 and 'cooler' cells 118 are only two of the many suitable forms of pretreatment that now exist; doubtless other forms will hereafter be developed. Any devices or methods suitable for the purposes herein will serve.

Due to the short residence time of a single particle passing through the plasma, two separate ion handling (pretreatment) and mass separating techniques may be used.

A gain of two orders of magnitude relative to current ICP-TOF-MS instruments, which means about one order of magnitude greater than current quadrupole systems is also desired. The mass spectrometer-based flow cytometer is ideal for the detection of heavy atom tags. It is sufficient to determine only the mass range above ca. 100 amu. One of the most significant impediments to improved sensitivity is space charge repulsion of the dominant $Ar^+$ ions (m/z=40). Since the method is not limited by the conventional elemental analysis demands (the mass range of the typical elemental analyzer is from m/z=4 to m/z=250), it is possible to optimize the ion optics for the transmission of high mass ions.

While a conventional ICP-MS having simultaneous detection capability (for example, an ICP-TOF-MS 126 or ICP-ion trap-MS) is as a detector of the MS FC 101, it should be realized that the requirements of the MS FC 101 are quite distinct from those of the conventional elemental analysis application. In particular, in the MS FC application the elements to be determined (as tags or labels) can be selected with advantage to be those above, say, 90 atomic mass units (amu, dalton, Thomson). In such instance, there is no need to provide simultaneously optimum sensitivity for low mass (e.g., Li, B, Na, Mg, Co, etc.) and high mass (e.g., the lanthanides and noble metals).

One approach employing a TOF analyzer 126 is to accelerate the ion beam relatively early in the plasma expansion because an accelerated beam has a higher space-charge-limited ion current and to high-pass filter the beam. This can be through the use of a quadrupole-type device, which is not pressurized. The depleted ion beam can then be decelerated (even collisionally cooled in a pressurized multipole, which could potentially also provide ion-bunching) prior to injection into the TOF. It is anticipated that the space-charge limit of such a continuous extraction beam is sufficiently high to allow a ten-fold improvement in sensitivity for the higher mass ions.

An alternate, or concomitant approach, is to pulse-extract the ion beam. Since lower mass ions are accelerated to high velocity in a given extraction field, the Ar$^+$ ions (and lower mass ions, which can be discarded) run ahead of the higher mass ions of interest. Preferably, the front-running ions can be discarded using an orthogonal pulse, similar to "Smart-Gate" of the GBC TOF, (see, e.g., WO 98/33203) but in the ion optics region. The transmission window does not need to be precisely defined in this instance, as it is sufficient to intercept ions <100 amu. A downstream cooling cell could still be used to bunch the ions and normalize their energies. If the orthogonal pulser is problematic, the entire pulse-extracted ion beam can be run into the TOF extraction region, with the deficiency that more-narrow mass windows will be simultaneously injected into the TOF. Simple calculations (which overestimate the potential by at least some margin) indicate that a 15% duty cycle pulse-extractor could yield up to 28-fold (m/z=100) and 12-fold (m/z=238) sensitivity improvement over current (80 Mcps/ppm) quad systems. This assumes 100% transmission efficiency through the ion optics and 100% duty cycle of the TOF (requiring bunching).

The ion pretreatment device may also include a particle event trigger, which triggers instrument mass selection and detection systems to acquire data from discrete particles, and keeps the instrument idle between events. As is known to those skilled in the art, this can be done in many different ways.

Therefore, the ion pretreatment device may comprise:
a vacuum interface;
a high-pass mass filter downstream of the vacuum interface; and
a gas filled ion cooler cell downstream of the vacuum interface.

Among the distinctions that simplify the design of the MS FC 101 according to the invention relative to a conventional elemental analyzer are the relative invariance of the sample (cells or beads in a known buffer) that simplify the need for an ionizer design (e.g., ICP) that is tolerant of various sample types and matrices, the relative (with respect to the total ion current of the ICP) invariance of the total elemental composition of the sample that relieves the need to provide compensation for inter-element matrix suppression effects (recognizing that, for example, Na and Ca will be significant components of cells), and to a large extent (depending on the selection of tag elements) the need to compensate for the presence of spectral interferences due to argides, oxides and doubly charged ions. Thus, MS FCs according to the invention can be advantageously adapted to suit the cytometric application but not for the general elemental analytical application because of the selectability of the elements to be determined. For example, conventional elemental analysis by ICP-MS is compromised by the mutual repulsion of ions following extraction into the vacuum system; this space charge effect, well known to those skilled in the art, derives principally from the overwhelmingly large flux of lower mass ions that derive from the plasma support gas or the sample solvent such as O$^+$, Ar$^+$, ArO$^+$, Ar$_2^+$, and in some instances lower mass ions that derive from other sample matrix components such as Na$^+$, Ca$^+$, Cl$^+$. It will be recognized that the most significant of these ions that form the bulk of the space charge effect are low mass ions, being below about 80 amu. Thus, advantage is to be had by eliminating such low mass ions as early as possible following extraction into the vacuum system because doing so will alleviate the space charge and its associated effective potential field barrier that suppresses transmission of other ions. Several schemes for achieving this relief can be conceived, including the use of a high-pass mass filter such as a quadrupole device that is operated to transmit ions above, say 80 amu. Notably, a quadrupole can be operated at the pressures extant in the ion optics region (typically about 10$^{-3}$ torr). An additional advantage of such an ion pretreatment device for the present application is that it can also be operated to simultaneously provide a low pass mass filter function (that is, a bandpass between a selected low mass and a selected high mass). In the instance that a time-of-flight mass analyzer is used, this bandpass can provide an improvement in duty cycle (resulting in improved sensitivity) because it minimizes the incursion of the arrival of high mass ions from a previous pulse into the arrival time distribution of the current pulse and also the incursion of low mass ions from the previous pulse into the arrival time distribution of the current pulse (where "pulse" means the packet of ions that are injected into the flight tube of the time of flight mass analyzer). Further, acceleration of the ions as soon as possible upon their entrance to the vacuum system (or near the point where the debye length of the plasma is comparable to the dimensions of the apparatus or lenses) can further mitigate the space charge effects. However, in the instance that the ions are subsequently decelerated (for example, in the acceleration region for the TOF), the space charge effects can return and reassert themselves resulting in reduction of sensitivity and, in the instance of the TOF, reduced mass resolution due to energy broadening in the direction of the flight tube. Hence, the high pass mass filter, which can be functional at relatively high ion kinetic energy if appropriately designed, can be operated in concert with acceleration optics to mitigate space charge effects both immediately downstream of the vacuum interface and further downstream, for example in the acceleration region of a TOF mass analyzer 126.

It is further advantageous, as is well known to those skilled in the art, that reduction of the axial ion energy by collisions with a non-reactive buffer gas in a pressurized multipole cell (a "cooler" cell) 118 provides improved resolution and sensitivity for TOF mass analysis (also expected to be true for an array-detector magnetic sector mass analyzer). Here again, the high pass mass filter 116, which should precede the "cooler" cell 118, can be operated in concert with the "cooler" cell 118 with advantage, since bandpassing the ions prior to the "cooler" cell 118 will mitigate to large extent space charge effects that otherwise would be detrimental (i.e., cause loss of sensitivity) in the "cooler" cell (which would happen because the ions are slowed by collisions in the "cooler" cell, and slowing them without first removing the bulk of the low mass "space charge inducing" ions causes an abrupt appearance of a significant defocusing space charge field near the entrance of the "cooler" cell).

As is known to those skilled in the art, in certain instances advantage is also to be had in including reactive gases in the "cooler" cell 118 in order to transform ions that are isobaric and thus are interfering or are interfered (reference U.S. Pat. No. 6,140,638). Further, the "cooler" cell can also be operated in a trap-and-pulse mode that could be optimized for synchronous operation with a TOF acceleration pulse to provide improved duty cycle (and hence sensitivity) for that mass analyzer. Thus, the MS FC 106 can incorporate with advantage ion acceleration optics and a high pass mass filter.

For several mass analyzer embodiments, including in particular the TOF and array-detector magnetic sector configuration, the use of a gas-filled "cooler" cell is also advantageous. For the TOF configuration in particular, the high pass mass filter could with advantage be operated as a bandpass mass filter with both a low and a high mass transmission limit. As is known to those skilled in the art, the high pass mass filter and "cooler" cell can be combined as a single unit (cf., U.S. Pat. No. 6,140,638).

Advantage is also to be had, to minimize the volume of data collected to include only the most significant data or, in the instance of a mass analyzer (such as TOF) which is constrained by a duty cycle, to coordinate the measurement of data with the passage of a particle of interest through the detector system. In the conventional FACS method, this coordination is accomplished most often by the measurement of light scattering as the particle passes through the excitation region; the nature of this light scattering (forward and side light scatter) can provide information on the size and granularity of the particle which also has diagnostic value. In the MS FC or OES FC method, light scattering can be similarly used.

Where the source of excitation is an ICP, the scattering event can be detected prior to vaporization of the particle; hence a delay corresponding to the time or spatial delay required for signal generation. For OES FC this is the time or distance required for vaporization, atomization, ionization and emission; for MS FC an additional delay corresponding to the transit time of the extracted ions from the region of ionization to the mass analyzer is required. Those skilled in the art will realize that for continuous monitoring mass spectrometers, for example an array detector magnetic sector mass analyzer, this delay should be applied to the arrival of the ions at the array detector. For other mass analyzers, for example TOF and ion traps, the delay is applied to the device that introduces the ions into the mass analyzer, for example the acceleration region preceding the flight tube of the TOF or a pulsing lens that introduces ions to an ion trap, to which the subsequent mass analysis and detection is synchronized.

Other methods of providing a trigger for data collection are contemplated for the MS FC 106. For example, it is expected that the passage of a particle through the ionizer (for example, the ICP) will cause an abrupt and consequent change in the mass distribution of the major ions that are extracted (for example, the dominant $Ar^+$ signal in ICP-MS could be suppressed with concomitant formation of $C^+$, $^+$, $Na^+$, $Ca^+$, etc.). It is thus expected that the ion current ejected or the spatial position of this ion current ejection (due to differences in the stability characteristics of ions of different masses) from, for example, the high pass mass filter, will change significantly and can be detected with one or more electrodes within or external to, for example, the high pass mass filter. Further, the magnitude or duration of the current change detected may be correlated with the size or content of the particle and could provide further diagnostic information.

Other trigger devices are contemplated, including, for example, a detector that measures changes in the ion current or impedance or magnetic field associated with the ion beam extracted into the vacuum system.

Optionally, various components, including for example a high mass filter and a gas-filled ion cooler, may be provided in a single housing. This can provide, for example, improved durability, as well as improved operating, handling and installing qualities.

Mass Spectrometer

The pretreated ion cloud may be analyzed with a simultaneous mass analyzer. Sequential mass analysis (e.g., through the use of quadrupole devices) is also possible. Examples of simultaneous mass analyzers include TOF, 3D trap and Linear Trap.

In some instances where the MS FC 101 method is to be used to best advantage (e.g., multiplex assay of individual particles), a simultaneous mass analyzer is preferred. For example, in the instance of the use of an ICP as the vaporizer, atomizer and ionizer, the transient signals from a single particle may last for a period in the range 20 to 200 microseconds, which can be insufficient to allow quantitative multiplex assay using a sequential mass analyzer, for example a quadrupole mass analyzer. In such instances, examples of preferred mass analyzers include TOF, array-detector magnetic sector, 3D ion trap and linear ion trap. In other instances where the period of the transient signal is significantly longer, either by the nature of the device to vaporize, atomize and ionize or by broadening of the transient signal, for example through transport of the vaporized particles, atoms or ions through a length of tubing or through collisional processes (such as those reported by D. R. Bandura, V. I. Baranov and S. D. Tanner in J. Anal. At. Spect. 2000, V15, 021-928), a sequential mass analyzer may find utility.

At the current state of development of mass analyzers, the TOF appears to be best-suited for the MS FC application. Ion traps (3d and linear) might be suitable provided that they are preceded by a selection device, for example a high pass mass filter, that reduces the space charge in the trap. The array-detector magnetic sector analyzer, which offers high duty cycle and should provide high sensitivity, could be suitable provided that an efficient array detector is developed, though at the present state of development the abundance sensitivity (overlap of signals onto neighbouring mass channels) is limiting.

The most commonly-used mass analyzer 106 coupled to the ICP is at present the quadrupole, principally because of its robustness, ease of use, and moderate cost. However, the quadrupole is a sequential scanning analyzer having a cycle time for multiplex analysis that is long relative to the duration of a transient signal from a single particle in the plasma source. Therefore, the quadrupole cannot deliver correlated multi-analyte signals for such a short transient. A quadrupole ICP-MS analyzer is often used for the analysis of samples presented in quasi-continuous flow, for example for nebulization and laser ablation. It is appropriate for the analysis of homogeneous samples, such as for many conventional immunoassays where total element signaling is of interest.

In contrast, the time-of-flight (TOF) analyzer 126 shown in FIG. 2, which samples a packet of ions in a given time period and spreads them in time according to their velocities in a potential field which are a function of the mass-to-charge ratios of the ions, is a "simultaneous" analyzer that is suited to the analysis of short transients such as those produced by single particles. Although TOF analyzers are known, the inventors are unaware of any TOF or other mass spectrometer analyzer currently being used for flow cytometry. Commercial ICP-TOF-MS instruments are some 10-100 times less sensitive than quadrupoles, at least in part due to more significant space charge effects in the ion optics and TOF acceleration region and to inefficiencies in duty cycle. With the employment of appropriate ion optics and other concepts noted herein, these deficiencies should be alleviated.

Figure 3:
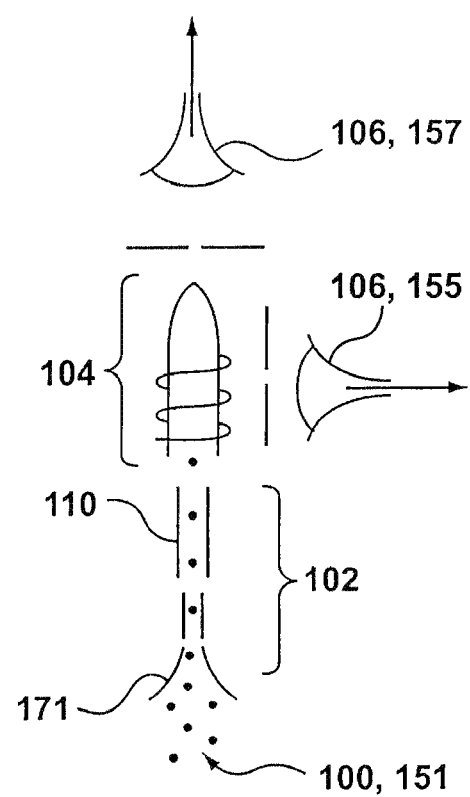
FIG. 3 is a schematic diagram of an embodiment of an optical emission spectrometer (OES)-based flow cytometer of the invention.

Another useful cytometer configuration is the OES FC 151 shown in FIG. 3. A distinction between the OES FC 151 and the MS FC 101 is that in the former, light emitted by both atoms and ions derived from the vaporized particle are collected and transmitted to an optical spectrometer having an array detector. In the ICP embodiment of OES FC 151, the emission may be collected either radially through the ICP at a specified "height" above the rf load coil (the preferred observation height is a function of the plasma conditions, but is stable for stable ICP conditions) or axially by looking "down" through the plasma towards the injector (which requires a cooled viewing interface usually with a curtain flow of gas), as shown in FIG. 3. The configuration and use of radial- and axial-viewed ICP-OES instruments is well known by those skilled in the art.

Among the distinctions of cytometers according to the invention from conventional fluorescence-based flow cytometry are that: (1) the cells or beads or analytes are tagged with elements rather than fluorophores; (2) the cells or beads are vaporized, atomized and (optionally, but usually naturally under optimum conditions) ionized and it is the elemental components of the cells and beads that are detected; (3) excitation to induce emission is gained from the ICP (convective and/or electron impact heating) rather than laser excitation at an absorption band of the fluorophore; (4) almost all elements of the periodic table are excited to emission (either atomic or ionic) under the operating conditions of the ICP, whereas multiple fluorophore excitation in conventional flow cytometry generally requires two or more excitation lasers, each of which may excite one or more fluorophores with absorption bands that are coincident with the wavelength of the excitation laser; (5) the emitted light is dispersed by, for example, eschelle gratings or prisms in one or preferably two dimensions and collected on an array of detectors, for example a CCD "camera", whereas the conventional flow cytometer uses bandpass optics to select a "least interfered" wavelength for each fluorophore; and (6) the emission wavelengths are more narrow in ICP-OES than in fluorescence-based flow cytometry, and there is usually more than one usable and detectable wavelength so that inter-element interferences are both less common (better resolved emission spectra) and more easily circumvented (by choosing an alternate emission wavelength).

EXAMPLES

Example 1—Development of Aptamers for Specific Labeling Leukemic Stem Cells

Leukemic stem cells and their progenitor cells can be purified [10]. They can be used as targets for selection of aptamers by selecting for the stem cell and against the progenitor cells using a novel method of combinatorial screening. The selected aptamers can be tested for, and selected against cross-reactivity with other aptamers directed for the multiplex assay of the challenge. The aptamers can be labeled with distinguishable stable isotopic elemental tags as is known to those skilled in the art.

Example 2—Preparation of Labeled MO7E Cell Line

A homogeneous MO7E cell-line which has been transduced with the p210 bcr/abl tyrosine kinase fusion protein from chronic myeloid leukemia can be used. This cell expresses the CD33 surface marker as well contains large amounts of p210 internally. The markers can be tagged with antibodies or aptamers suitably tagged with commercially-available tagging kits (NanoGold™, DELFIA™). The tagged affinity products can be incubated with fixed, permeabilized cells.

Example 3—Preparation of Quadrupole ICP-MS-based Flow Cytometer

Demonstration of concept can be achieved using a quadrupole-based ICP-MS and the tagged cells of Example 2.

A flow cell can be constructed based on a direct injection nebulizer or a sheath-flow non-ionizing nanosprayer. A commercial flow cytometer can be used, but with modifications, and excluding parts related to fluorescence.

Single ion monitoring at the mass/charge of one of the tag elements has improved duty cycle relative to scanning mode so that many of the cell events are, observed. Subsequent measurement, in the same sample but at a later time, at the second surface tag element mass/charge will confirm independence of the affinity chemistry and detection, with the implication that simultaneous determination with an appropriate (TOF) detector is possible. Observation of the internal protein marker will provide important evidence that cell volatilization is achievable. If the internal marker is not detectable, in-line lysis can be used.

Example 4—Development of a Prototype Single Particle Injector

Figure 4:
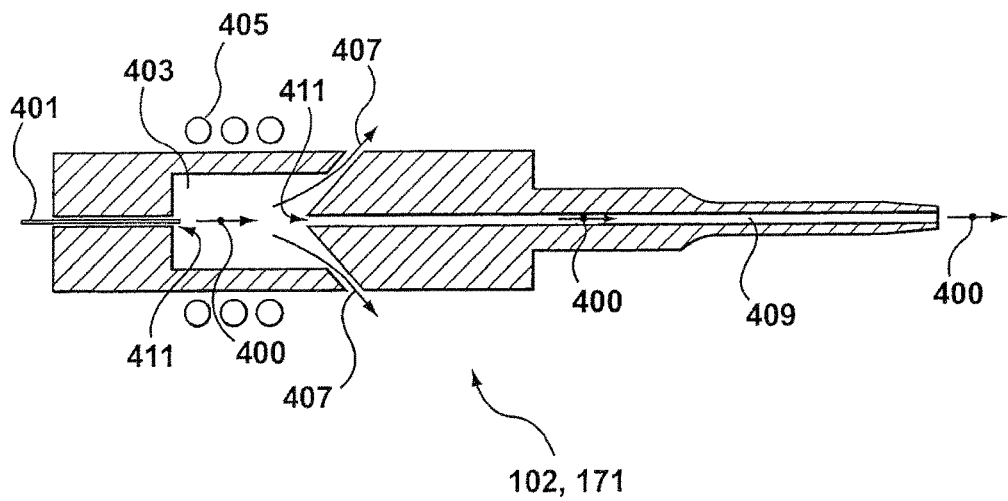
FIG. 4 is a schematic diagram of a single-particle injector according to the invention.

Referring to the injector 171 shown in FIG. 4, the injector is used to inject cells (or beads or other particles) 400 together with the buffer solution into the desolvation chamber 403 surrounded by a heater 405. The buffer solution flow is nebulized by high-pressure gas. The volatile component of the buffer and cells (mostly water) is transferred from aerosol to gas phase during the desolvation process and is expelled out of the desolvation chamber together with most of the nebulizer gas through exhaust vents 407. In most cases, the nebulizer gas flow is limited by size and design of the injector (nebulizer). Therefore, some makeup gas can be introduced to allow complete desolvation. Desolvated heavy cells (or beads) escape directly into the straight cylindrical channel 409 with the rest of the gas and are introduced into vaporizer/atomizer/ionizer 104 of the EFC. In an embodiment the vaporizer/atomizer/ionizer is the ICP plasma, which allows .˜1 l/min of gas to be introduced. Therefore, by adjusting the gap 411 between the desolvation chamber and the cylindrical channel housing, one can control desolvation as well as flow into the ICP plasma.

Example 5—Preparation of ICP-TOF-MS-based Flow Cytometer Research Prototype Instrument ICP-TOF-MS instruments are commercially available. The TOF mass spectrometer provides a simultaneous analyzer which is beneficial for mulitvariant analysis, of for example, rare leukemic stem cells.

An ICP-TOF-MS can be outfitted with a flow cell. The components of the instrument as shown in FIGS. 1, 2, and 3 and described in the preferred embodiment can be assembled. Relevant components of commercial products (ELAN® ICP-MS and prOTO® orthogonal MALDI-TOF) can be procured as the basis of a working system. Some modification of the operating system will be required to address the specific data collection issues of the cytometer prototype; suitable modifications are well understood by those of ordinary skill in the art. It can be sufficient to operate independent computer control systems for the ICP source and the TOF analyzer, as this would allow rapid and efficient research investigation.

An instrument can be evaluated with respect to its analytical performance for homogeneous aqueous sample introduction as well as homogeneous cell digests. The ICP-TOF MS-based flow cytometer can be tested, for example, using human established leukemia cell lines (MO7e, K562, HL-60) to investigate the capabilities with respect to the needs for the cytometric application. Specifications for dynamic range, abundance sensitivity, transient signal pulse width and detection mode (analog/digital) for the research prototype instrument can be established.

The following examples have been demonstrated using a conventional quadrupole ICP-MS instrument (sequential scanning) using conventional nebulization of solutions obtained by acidification with HCl of the sample following immunoprecipitation and washing, which digested the sample yielding a relatively homogeneous solution. Thus, "simultaneous" determination refers in this instance to simultaneous immunoprecipitation followed by sequential measurement of the concomitant tags by ICP-MS.

Example 7—Dynamic Range of Anti-Flag M2 Agarose Bead Element-Tagged Immunoassay

Figure 5:
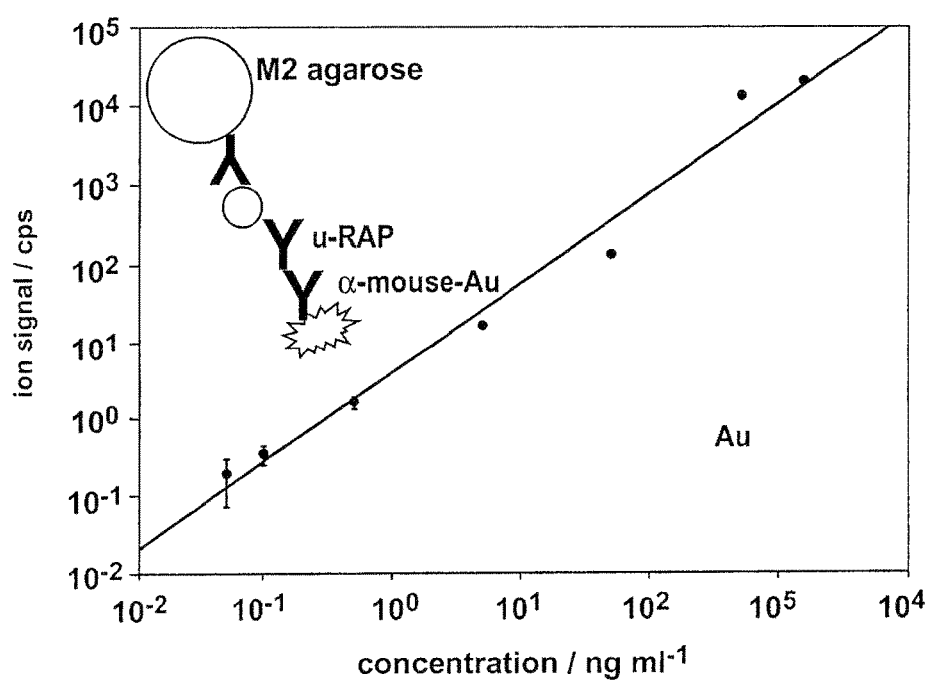
FIG. 5 is a calibration curve for flag-BAP using agarose bead immobilization with α-BAP primary and Au-tagged α-mouse secondary antibodies.

FIG. 5 is a calibration curve of the ICP-MS linked immunoprecipitation assay of 3.times.FLAG-BAP. M2 agarose beads were used to capture samples of serially diluted 3.times.FLAG-BAP over a concentration range of 0.05 ng to 1500 ng per 100 µl 3×FLAG-BAP was detected using an anti-BAP primary antibody and an anti-mouse-nanoAu secondary antibody. Diluted HCl was used to dissolve the nanogold tag for ICP-MS sampling. The results indicate that the detected signal (for gold) is linearly proportional to the antigen (FLAG-BAP) concentration, and that at least 4.5 orders of magnitude of linear dynamic range are achievable. Large dynamic range is important in the cytometric application to permit simultaneous determination of biomarkers that appear in largely different copy-counts per cell or bead.

Example 8—Simultaneous Assay of Two Cytokines Using Beads

Figure 6:
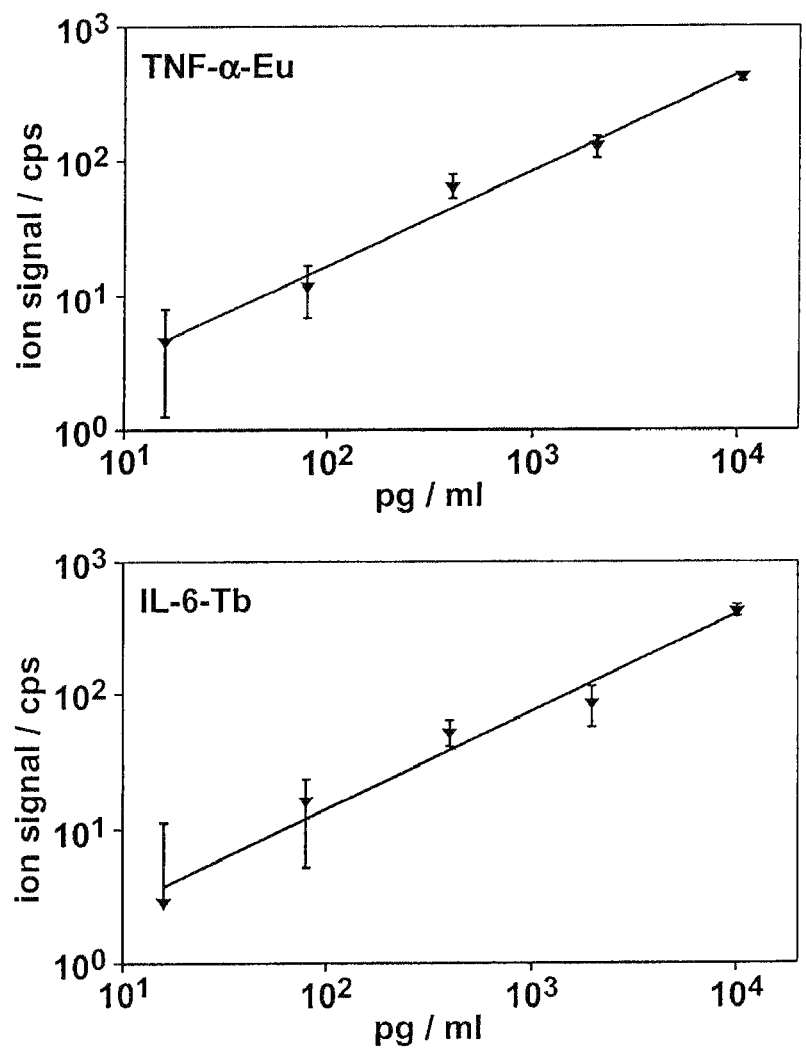
FIG. 6 is a plot of Fluorokine bead assay, detecting TNF-.alpha. and IL-6 simultaneously using distinguishable (Eu and Tb) elemental tags on the corresponding primary antibodies.

Fluorokine™ beads coupled with cytokine capture antibodies against either TNF-α. or IL-6 were mixed and exposed to a mixture of cytokines, including TNF-α. and IL-6, incubated and then probed with cytokine-specific antibodies tagged with Eu (for anti-TNF-α.) and Tb (for anti-IL-6). After washing and digestion with HCl, the solution was analyzed for Eu and Tb. FIG. 6 provides calibration curves derived from this simultaneous immunoassay experiment. Linearity of signal with antigen concentration over at least 3 orders of magnitude is observed.

Figure 7:
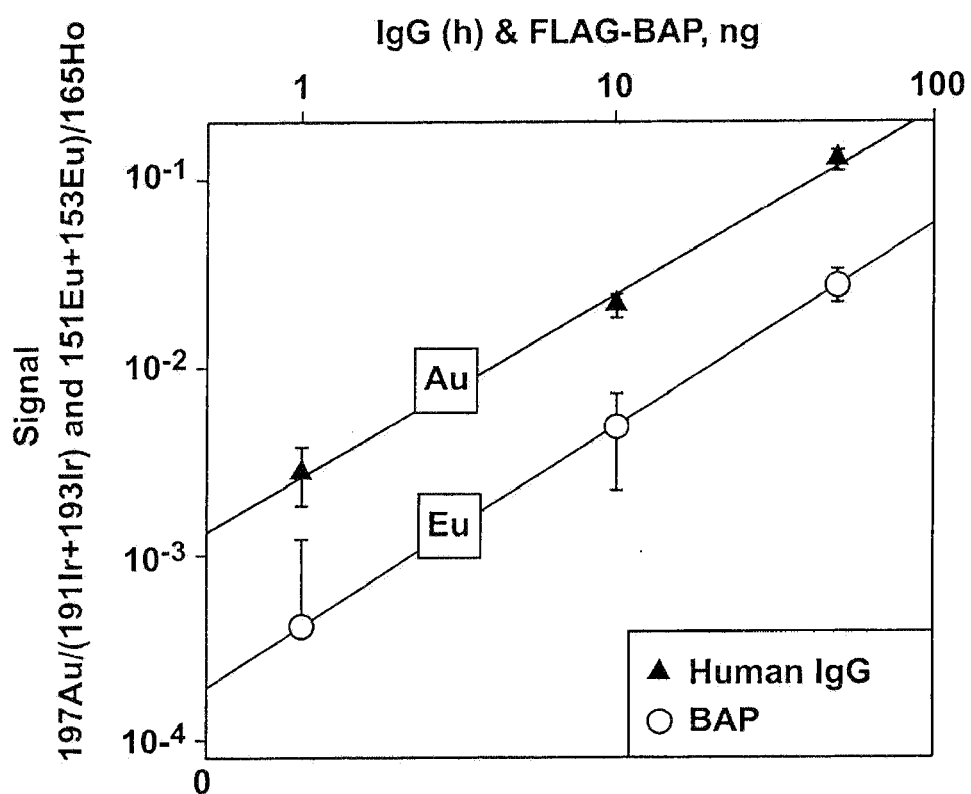
FIG. 7 is a plot of an ELISA based assay coupled to ICP MS showing the simultaneous quantitation of two proteins.

Example 9—Simultaneous Assay of Two Proteins Using ICP-MS-Linked Maleylation Immunoassay FIG. 7 shows the simultaneous quantitation of two proteins using a direct immunoassay conducted in a Reacti-bind Maleic Anhydride 96 well plate, coupled to ICP-MS detection. In this experiment, two proteins (Human IgG and 3×FLAG-BAP) in 1×PBS were incubated in triplicate for one hour at room temperature to allow binding to the surfaces of the well of the Maleic Anhydride plate. Negative controls consisted of 100 µl PBS without protein. The plate was probed with primary antibodies anti-Human Fab'-nanoAu and anti-FLAG-Eu, washed and acidified with 10% HCl with 1 ppb Ir and 1 ppb Ho as internal standards [11]. Homogeneous samples were used wherein the elemental tag(s) are released to acidic solution for conventional nebulizer introduction to the ICP-MS. Note that the sensitivity to IgG using the nanogold tag is approximately 10 times greater than that for FLAG-BAP using the Eu tag; this is because each nanogold tag contains approximately 70 gold atoms (Au is monoisotopic) while each Eu tag contained only between 6 and 10 Eu atoms, approximately equally distributed between the two natural isotopes of Eu ($^{151}$Eu and $^{153}$Eu, the sum of which were measured). The example demonstrates that at least two proteins can be immunoreacted simultaneously and detected without mutual interference, and that the sensitivity scales with the concentration of the antigen and with the number of atoms of the measured isotope per tag.

Example 10—Preparation of a Kit for the Analysis of an Analyte Bound to a Single Cell by Mass Spectrometry A kit is assembled comprising (1) a tagged biologically active material which binds to an analyte of interest bound to a single cell and (2) instructions for single cell analysis by mass spectrometry.

Example 11—Forensic Applications

The methods and apparatus of the present invention can be used for forensic applications. For example, the methods and apparatus can be used to:

determine antigenic blood types (ABO and Lewis types); identify body fluid (blood, semen, saliva) and other biosamples (whole blood, plasma, serum, urine, cerebrospinal fluid, vitreous humor, liver or hair);
determine tissue origin (species, personal identity, etc.);
determine paternity.

Example 12—Transfusion Medicine

The methods and apparatus of the present invention can be used in transfusion medicine to:

resolve blood group A, B and D typing discrepancies; determine the origin of the engrafted leukocytes in a stem cell recipient; and determine the origin of lymphocytes in a patient with graft-versus-disease.

Example 13—Flow Cytometer with ICP-MS Detector Feasibility Test

We have performed feasibility studies to validate the concept of the present invention. A quadrupole (sequential mass scanning) ICP-MS instrument designed for conventional elemental analysis (and thus not optimized for the flow cytometric application) was used. The instrument was modified in only two ways: a modified sample introduction system was installed, and an oscilloscope was attached in parallel with signal handling hardware and software of the original detector system.

Figure 8:
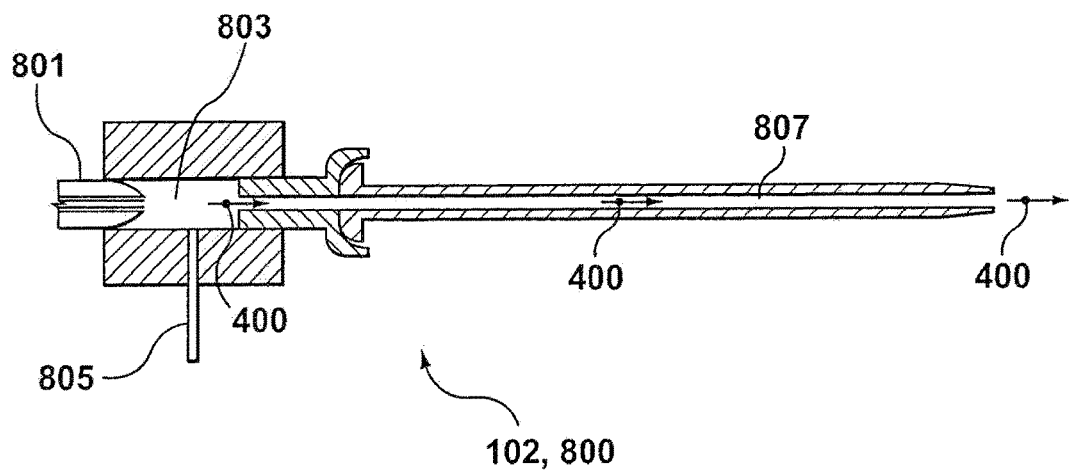
FIG. 8 shows a schematic diagram of a sample introduction system

The sample introduction system 102, 800 is shown schematically in FIG. 8. Sample 400 consisting of cells or other particles was aspirated using a syringe pump connected with capillary tubing 801 to a small volume spray chamber 803 having a drain 805 to remove condensed liquid and having no gas outlet except into the ICP through the 2 mm diameter injector tube 807. Sample was pumped at 50 µL/min, about half of which was drained from the spray chamber 803 and half delivered to the ICP. The inventors recognize that this sample introduction device 800 may not necessarily optimum for presentation of single particles to the ICP with high efficiency in all cases, depending upon the circumstances of the analysis, but it was sufficient in this case to introduce at least a fraction of the particles into the ICP and thus to show feasibility.

The discrete dynode detector of the ICP-MS instrument provides signals that are either analog or digital (pulse). The analog signal, taken part way along the dynode chain, is converted to digital output in the hardware and software of the detector system. The digital (pulse) signal is taken from the final dynode of the chain, is amplified and transient signals corresponding to single pulse events whose amplitudes exceed a given threshold are counted in the detector system hardware and software. The detector system hardware and software can be configured to provide output not of each pulse, but the integral of these over a specified measurement period (minimum about 100 microseconds). In normal operation, if the signal detected at the analog dynode exceeds a specified threshold, the dynode chain downstream is disabled (disabling digital signal detection). If the analog signal is higher than a second threshold, the detector firmware adjusts the voltage of the ion optics of the instrument to defocus the ions from the detector in order to protect the detector. An oscilloscope was tapped into the analog output and operated in parallel with the detector hardware to enable the measurement of the transient events over the period of a single particle event in the ICP (e.g., up to several milliseconds with as low as a few nanoseconds resolution).

Because the instrument used for these experiments is not capable of measurement of more than one mass/charge channel during a short transient period, multiplex analysis of a single particle event in the ICP was not be demonstrated. However, measurement of single mass/charge detection channel events has allowed demonstration and evaluation of certain important characteristics of the ICP-MS detector system for the cytometric application. The inventors believe that these characteristics can be replicated, with some differences depending on the selected embodiment of the instrument configuration, with a simultaneous mass analyzer, with the additional benefit of facilitation of simultaneous measurement of many mass/charge detection channels permitting multiplex assay of single particles.

Feasibility Test 1: Detection of Single Particle Events, and Estimate of Sensitivity of Current Instrument The MO7e cell line is a human megakaryocytic leukemia-derived cell. MO7e expresses CD33 antigen (67 kDa single chain transmembrane glycoprotein, myeloid cell surface antigen CD33 precursor (gp67)). The cell is thought to express approximately 5000 to 10000 copies of antigen per cell. The cell line was used to demonstrate that individual cells can be observed by methods according to the invention, and to estimate the sensitivity of such method using the current instrumentation. The CD33 surface marker was detected using monoclonal anti-CD 33 (IgG1 mouse) and Nanogold™-tagged anti-mouse secondary antibody (approximately 70 Au-atoms per tag). It is estimated that the efficiency of secondary antibody staining is approximately 10%.

Materials

MO7e cells were cultured for three days in a T75 flask. The cell concentration was determined by hemocytometer and found to be $0.5 \times 10^6$ cells/ml.

Monoclonal antibody anti-CD33, unconjugated. IgG1 (mouse) isotype supplied at 2 mg/ml and purified in PBS/BSA with 0.1% sodium azide by Immunotech Inc. Cat#1134.

Secondary anti-mouse IgG conjugated with nanogold from Nanogold Inc. (approximately 70 Au-atoms per tag)

1% formalin prepared from 37% formalin; diluted in PBS.

Wash and antibody dilution buffer PBS/1% BSA.

50 mM ammonium bicarbonate buffer, pH 8.0.

Procedure

Tubes were soaked in PBS/1% BSA for one hour. MO7e cells were pelleted at 1500 rpm (at approximately 200 g) 5 min, resuspended in 5 ml PBS, pelleted and the wash discarded.

Cell pellet was resuspended in 3 ml PBS/1% BSA and distributed into three eppendorf tubes (at approximately 106 cells/tube) marked as primary and secondary antibodies added; only secondary antibody added; or no antibodies added.

Primary antibody was diluted 1:50 in PBS/1% BSA and added to the cell pellet for 30 min on ice.

Cells were washed with PBS/1% BSA once.

Secondary antibody was diluted 1:50 in PBS/1% BSA and added to cell pellet for 30 min on ice.

Cells were washed once with PBS/1% BSA, once with PBS.

Live stained cells were fixed in 1% formalin/PBS for 10 min RT and left in the fixative on ice overnight.

Cells that did not receive antibodies were treated only with PBS/1% BSA concordantly with the stained cells.

Stained formalin fixed cells were pelleted at 1500 rpm (at approximately 200 g) for 5 minutes and resuspended in 1 ml 50 mM ammonium bicarbonate buffer, pH 8.0 per tube next day. This was discarded after centrifugation and fresh bicarbonate (0.5-1 ml) was added to each tube.

Tubes were vortexed gently to break up the pellet, left to sit for 5 minutes for large clumps to settle to the bottom, and the top 25 μL of whole cell suspension were injected into the ICP-MS instrument.

Observations

The integrated (pulse detector) signal for Au for discrete cell introduction gave 300-500 counts per second (cps), secondary antibodies only, less than 100 cps, no antibodies, less than 10 cps and buffer only, less than 3 cps.

Figure 9:
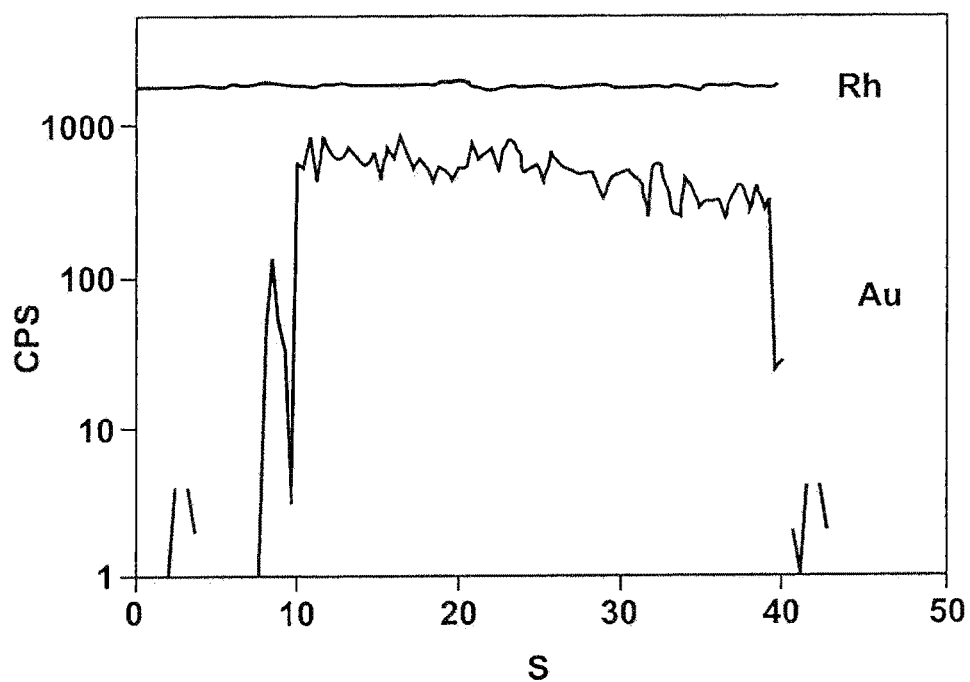
FIG. 9 shows overlaid results of measuring ion signals as a function of time for direct injection of a standard solution of 100 ppt Rh (1% $HNO_3$) and of a MOTE cell suspension for which the surface antigen CD33 was tagged with a Au particle.

FIG. 9 shows the overlaid results of separate direct injections of the 100 ppt Rh (1% HNO3) and cell suspension (separate injection, 50 mM NH4HCO3) samples as described above.

Figure 10A:
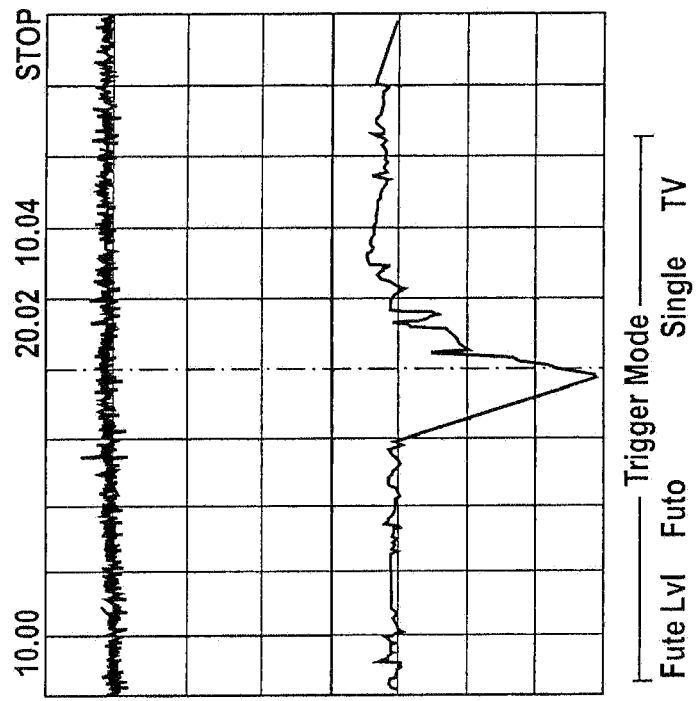
FIG. 10A shows oscilloscope output of an $Ar_2^+$ signal from MO7e cell introduction for which the surface antigen CD33 was tagged with a Au particle.
Figure 10B:
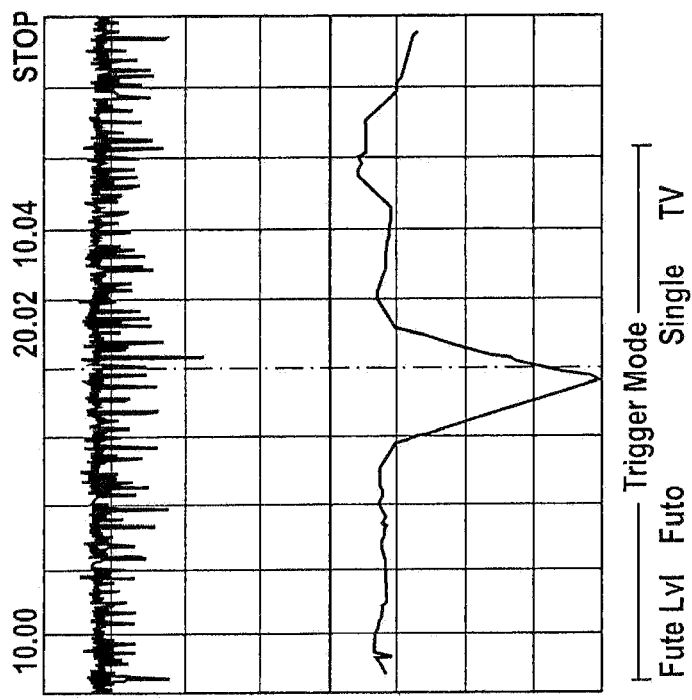
FIG. 10B shows oscilloscope output of an $Au^+$ signal from MO7e cell introduction for which the surface antigen CD33 was tagged with a Au particle.

FIGS. 10A and 10B show oscilloscope data associated with FIG. 9. FIG. 10A (on the left) shows the signal for $Ar_2^+$ (about $10^7$ cps) signal. The upper trace covers a relatively large time window (ca. 100 μs), from which one could conceivably determine the average ion signal rate. The lower trace shows the pulse for a single ion detection event (over a greatly magnified time scale). FIG. 10B (on the right) shows $Au^+$ from cell introduction. The upper trace indicates that multiple ion signal pulses are not observed. The lower trace shows the signal pulse for a single Au ion detection event. Typically, only one ion pulse was observed in a particle event time window, suggesting that we detect on average only about one Au atom per cell.

Efficiency of Detection

We estimate the sample introduction rate at (very) approximately 400 cells/second, derived as follows: approximately $1 \times 10^6$ cells per sample, 1 mL/sample at 50 μL/minute introduction sampling with 25 μL/min delivered to the ICP.

Accordingly, we infer that approximately one Au atom per cell is observed.

The detection efficiency of the instrument used was estimated from the signal obtained from continuous aspiration of a sample containing 100 parts per trillion (ppt, mass/volume) in 1% nitric acid. The signal obtained was approximately 2000 cps, suggesting an efficiency for detection of Rh of $1\times10^{-5}$, derived as: 100 ppt ($10^{-10}$ g/mL), atomic weight 103 g/mole, 25 µL/min delivered to plasma, yielding $2\times10^8$ atoms Rh/second delivered to plasma for which 2000 cps is observed. The inventors ascribe this efficiency to the following: 100% ionization, 1% transmission through the vacuum interface (100% of central plasma containing ion inhaled through sampler, 1% of sampler flow transmitted through skimmer), 10% transmission through mass analyzing quadrupole, and therefore about 1% transmission through the ion optics. (From these estimates, we infer that improvements in sensitivity for the cytometric application, assuming retention of the vacuum interface configuration, should principally focus on improving the transmission through the mass analyzer (e.g., TOF with high duty cycle) and, more importantly, the ion optics (according to the earlier discussion, principally through accelerating optics and elimination of space-charge-inducing ions)).

Therefore, if one Au atom detection event per cell is obtained, and this is obtained with the same detection efficiency as Rh solution, we estimate that the MO7e cell averages approximately 1400 tagged CD33 markers per cell. With the assumption that the efficiency of the two antibody tagging is about 10%, the estimated number of CD33 per cell is 14000, which is consistent with the 5000-10000 quoted earlier. It is desirable to provide higher sensitivity so that proteins of lower copy-count per cell can be detected. In addition to the ion optical improvements suggested above, direct immuno-tagging (as opposed to the 2 antibody sandwich used here) is expected to be advantageous.

We conclude that the method is able to detect single particle events in the plasma. The experiments described provide guidance for research efforts to improve the sensitivity of the method. A simultaneous mass analyzer is required to facilitate the multiplex advantage that the mass spectrometer detector provides to flow cytometry.

Feasibility Test 2: Estimation of the Transient Period of a Single Particle Event The MO7e cell sample used in Feasibility Test 1 provides an opportunity for the estimation of the transient period of a single particle event, which is important for the design and optimization of the MS FC. It is estimated that the NaCl content in the cell is 0.9% w/w. For a 16 micrometer cell this converts to $2\times10^{11}$ atoms of Na per cell. The efficiency of the instrument used in these experiments for Na detection is lower than for Rh; about $1\times10^{-6}$. Thus, for a single cell event, $2\times10^5$ ions will reach the detector. This is a sufficiently-large number that the arrival period of Na ions corresponding to a single MO7e cell event can be measured. If the transient produced by the single cell event is of the order of 100-300 microseconds (as reported by Olesik for monodispersed 3-65 micrometer particles), an equivalent average count rate of $(0.7-2)\times10^9$ is achieved (with peak current about twice that).

FIGS. 11A and 11B show the Na$^+$ signal detected at the oscilloscope over the period of several cell introduction events. The data given in FIG. 11A shows the Na$^+$ signal when cells are introduced in a 30 mM CaCl$_2$ buffer. The data shown in FIG. 11B presents the results for buffer only. The variability of the observed signals may reflect the variability in cell size (volume and thus Na content) of the cell population, or might indicate the presence of Na-containing particles other than MO7e cells. The important observation, for the present purposes, however, is that the transient signal for a single particle event is of the order of 100-150 µs.

The baseline is very different between the two datasets shown in FIGS. 11A and 11B. This difference can be attributed to the fact that a first cell detected should trip the higher threshold detector protection circuitry and activate ion defocusing. This is because the anticipated 2×105 Na ions per cell arrive in the period of approximately 100-150 µs, which corresponds to an average count rate exceeding 109 per second, is sufficient to trip the second threshold detector. In the absence of cells in the sample (data given in FIG. 11B), the detector protection circuitry is not tripped. The ion optical defocusing appears to suppress ion transport by about a factor of 1000, accounting for the difference in the baseline data, but this is not intended to be a stable or reproducible (quantitative) defocusing factor.

Transient signals of 100-150 µs period, ascribed to MO7e introduction events, were observed at a frequency of about 5 to 6 per 10 milliseconds, or about 500 to 600 cells per second. This is consistent with the estimates made earlier, and with the estimate of 106 cells per 1 mL in the original sample (procedure step 4 of Feasibility Test 1, subsequently reduced to approximately 1 mL volume in step 9).

A notable inference taken from this experiment is that the high Na$^+$ signal anticipated for cells, or effects related to the change in mass distribution of the plasma ions as a result of the passage of a particle through the plasma, might provide a means to trigger the system upon a cell event. Further, it is feasible that the magnitude of the Na$^+$ signal (or signal of another element at high concentration in the cell), or the magnitude of effects related to the ion distribution change as a result of the particle's passage through the plasma, could be correlated with the physical size of the particle, which may be of importance in identifying target particles or distinguishing single particles from groups of particles.

The important conclusion of this experiment is that the transient signal is approximately 100-150 µs FWHM in duration. This has implications for design considerations to provide dynamic range. Further, it is evident that particles characterized by transient signals of this period can be introduced to the system at a rate of about 3000 per second (so that signal corresponding to a particle is present up to 50% of the time). Smaller cells, and smaller beads, should have shorter transients, and thus allow higher rate of introduction.

Feasibility Test 3: Comparison of Current FACS With the Current ICP-MS With Cell Injection, and Demonstration of Entire Cell Volatilization The inventors have had an opportunity to compare directly the performance of a current FACS instrument to that of the ICP-MS instrument with cell injection described in Feasibility Test 1. Further, the test was configured to provide for tagging of intracellular proteins; if these internal tags can be detected, this implies that the entire cell and its contents were vaporized, atomized and ionized, rather than just vaporization of surface tags.

Because the ICP-MS instrument used for these experiments was not a simultaneous detector, the same (nanogold) tags could be used for each antigen, and immuno-tagging was performed in separate vials for each sample and antigen. Thus, each antigen for each sample was determined in a separate analysis. Samples were introduced to the ICP-MS as described in Feasibility Test 1.

Preparation of Samples for ICP-MS Analysis with Cell Injection

Materials

Human Monocyte Cell Lines:

MO7e parent line is a human megakaryocytic leukemia-derived cell. MO7e express CD33 antigen (67 kDa single chain transmembrane glycoprotein, myeloid cell surface antigen CD33 precursor (gp67)). Approximately 5000-10000 copies of CD33 antigen per cell.

MBA-I and MBA-4 are stable clones of MO7e transfected with p210 BCR/Abl expression plasmid.

HL-60 (ATCC cat # CCL-240), myeloid leukemia cell line used as antigen in production of anti-CD33 monoclonal antibodies.

Antibodies:

anti-CD33, mouse monoclonal, unconjugated. IgG 1 (mouse) isotype. Supplied at 2 mg/ml purified in PBS/BSA with 0.1% sodium azide (Immunotech Inc. Cat #1134)

anti-IgG2a, mouse, (BD PharMingen, cat #555571) (0.5 mg/ml stock)

anti-BCR antibody raised in rabbit (Cell Signaling Tech. Cat #3902), used at 1:25 for flow cytometry Secondary antibodies: 2001 nanogold-anti-mouse IgG (NMI) and 2004 nanogold anti-rabbit Fab' (NRF) (Nanoprobes Inc.) used at (1:50) according to manufacturer's recommendation.

Buffers:

BD Biosciences FACS permeabilization solution 2 (cat #347692) PBS with Ca++/Mg++;

PBS/1% BSA

1% and 0.5% formalin prepared from 37% formalin; diluted in PBS 50 mM ammonium bicarbonate buffer, pH 8.0

Procedure:

Tubes were soaked in PBS/1% BSA for one hour.

Cells were pelleted at 1500 rpm(~200 g) 5 min, resuspended in 5 ml PBS and counted using a hemocytometer. Cell yield:

MO7e-1e6/ml
MBA-1-1e6/ml
MBA-4-1e6/ml
HL-60-1e6/ml

MO7e (tube #1) and HL-60 (tube #2) were stained live with anti-CD33 (1:50) on ice for 30 min; followed by one wash with PBS/BSA. Anti-mouse-IgG-Au (1:50) was added to the washed cell pellet for another 30 min on ice. Live stained cells were fixed in 1% formalin/PBS for 10 min RT and left in the fixative on ice over 48 hours.

MBA-I (tube #3), MBA-4 (tube #4) and MO7e (tube #5) were permeabilised and fixed in the FACS Permeabilization Solution 2 for 10 min at RT.

After one wash the cells were incubated in media with 10% FBS to block non-specific antigen sites for 15 min RT.

Permeabilized cells were treated with anti-BCR antibodies (1:25) (tubes #3,4,5) or with non-specific IgG (tubes #3°., 4°., 5°. w/o primary antibody) for 45 min RT. Secondary antibodies were added to washed cells anti-rabbit-IgG-Au (1:50) for 45 min RT.

Stained cells were washed twice prior to post-fixation in 0.5% formalin and kept in fridge over the weekend prior to MS analysis when the formalin was replaced with 50 mM ammonium bicarbonate.

Preparation of Samples for FACS Analysis (Carried Out Simultaneously With Above)

Materials

Antibodies:

anti-IgG 1-FITC mouse isotype, (BD PharMingen)

anti-CD45-FITC antibody raised in mouse (BD PharMingen) used at 1:50 for flow cytometry. CD45 is expressed on the surface of all human leukocytes. Used as a positive sample for FACS set-up.

Secondary fluorescent antibodies: anti-mouse IgG-FITC (BD PharMingen) and anti-rabbit-FITC (Biolab) used at (1:50)

Buffers:

BD Biosciences FACS permeabilization solution 2 (cat#347692)

PBS with Ca++/Mg++;

PBS/1% BSA

1% and 0.5% formalin prepared from 37% formalin; diluted in PBS 50 mM ammonium bicarbonate buffer, pH 8.0

Procedure

Cell preparation and primary antibody staining was done in parallel with samples for ICP-MS with 1e6 cells/ml/tube.

All procedures with fluorescent secondary antibody staining and cell washes were carried out in the dark on ice.

After the final PBS wash cells were resuspended in PBS (not formalin) and immediately processed by FACS (BD FACSCalibur).

Gates and settings were determined using the anti-CD45-FITC stained HL-60 as positive (R4) channel and isotype anti-mouse IgG-FITC stained HL-60 as negative (R3) channel.

Observations

Figure 12:
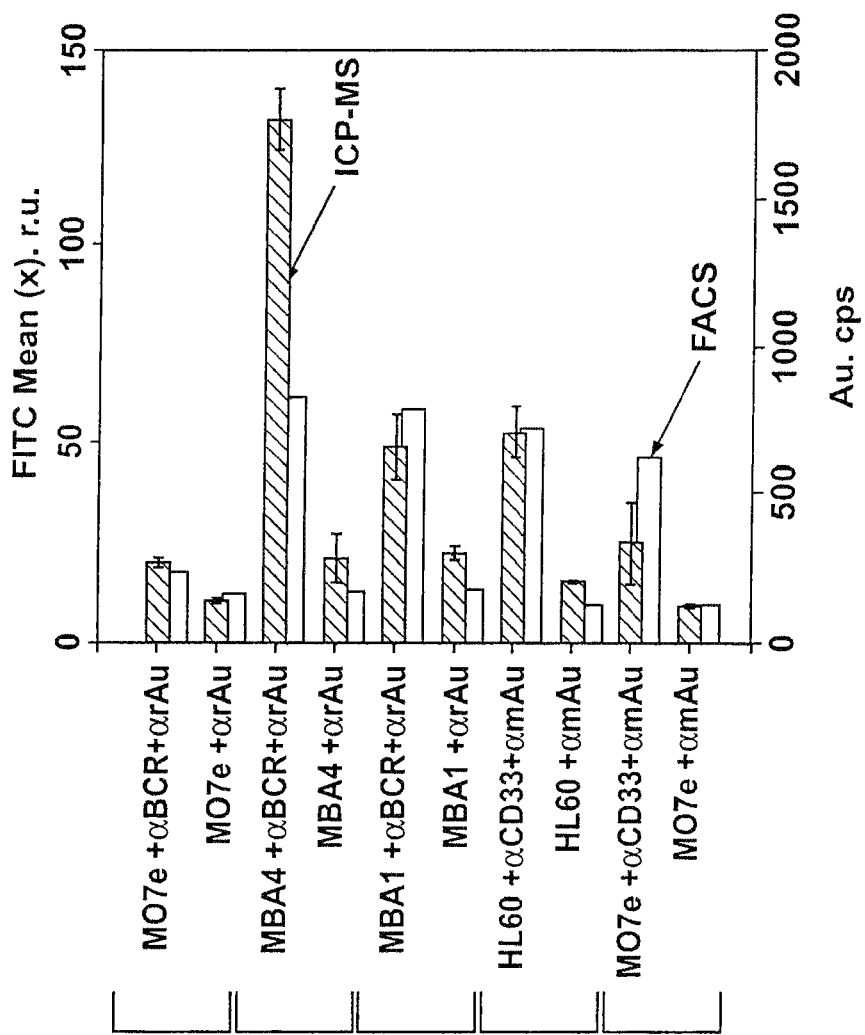
FIG. 12 shows comparative data for analysis of cell surface proteins and intracellular proteins by both conventional FACS and by the method of the present invention.

The results for both the ICP-MS detection (shaded grey) and conventional FACS (white) are summarized in FIG. 12.

Standard deviations for triplicate analyses by ICP-MS are shown by error bars; equivalent uncertainties for the FACS results were not provided.

Both the CD33 (surface markers on MO7e and HL60) and the BCR (internal marker in MO7e, MBA1 and MBA4) were determined by both FACS and ICP-MS detectors. This implies that the entire (permeabilized) cells and their contents were vaporized, atomized and ionized in the ICP-MS. Further, the FACS and ICP-MS results are largely in rather good agreement for both the surface and internal markers and for the procedural blanks.

We conclude from these results that FACS and ICP-MS detection (using the current un-optimized instrument) provide comparable results for single antigen assay. It is anticipated that the sensitivity of the ICP-MS detector will be improved as discussed above, and that incorporation of a simultaneous mass analyzer will permit high order multiplex assay. It is also evident that the MO7e, MBA1 and MBA4 cells used in these experiments were efficiently vaporized, atomized and ionized. This suggests that the optional in-line lysis device discussed above is not required for these or similar cells.

Feasibility Test 4: Production and Detection of Element-Tagged Beads

Another approach to multiplexed assay is to use different identifiable beads that immobilize antigens. The beads typically have capture affinity agents (e.g., antibodies) attached to their surface. After exposure to a sample, the bead-antigen complexes are typically exposed to a second affinity product (antibody, aptamer, etc.) which is tagged with an element or isotope as already discussed (herein, and in U.S. patent application Ser. No. 09/905,907, published under US 2002/0086441 on Jul. 4, 2002 and Ser. No. 10/614,115). The beads are distinguished by their elemental composition, which might be a surface element label, and encapsulated element label or an element label incorporated within the bead material. The identity of the bead can be associated with the type of capture affinity agent attached to the bead or to the sample (e.g., beads with different element labels are exposed to different samples, or are placed in different wells of a 96- or 384- or 1536-well plate). Thus, detection of the secondary affinity product tag determines the presence of the antigen and the element composition (element label) of the bead indicates which antigen was captured or the sample in which it was captured. The method is modeled after U.S. Pat. No. 6,524,793, assigned to Luminex, and references therein.

The beads may be of any appropriate material (e.g., polystyrene, agarose, silica). Each bead may contain one or more affinity capture agents, and multiplexed assay of the antigens captured on the bead may be conducted. The element label incorporated in or on the bead may be a single element or isotope or, preferably, a combination of elements or isotopes. For example, if the dynamic range of the detector is three orders of magnitude and differences in signal levels of a factor of three are reliably detected, two element labels can be combined in different ratios to provide 63 distinguishable beads. Under the same conditions, 5 element labels can provide 32,767 distinguishable beads. With 5 orders of dynamic range and 5 element labels for which factors of three in signal can be reliably detected, 248,831 distinguishable beads can be constructed. It will be recognized that the beads can be manufactured to a size suitable for complete vaporization, atomization and ionization in the device used for that purpose (e.g., ICP). It will also be recognized that smaller beads are likely to provide shorter transient signals, and that accordingly the rate of particle introduction can be optimized for the particular beads used.

To demonstrate the viability of the method, stober silica particles having a diameter of about 150 nm were grown in various lanthanide (Ho, Tb, Tm) solutions. The lanthanide elements were incorporated into the silica particles. The silica particles (beads) were introduced serially to the ICP-MS instrument as described in Feasibility Test 1. Since the instrument used was not capable of simultaneous multielement analysis, the transient signals for the lanthanides and for silicon were measured separately for different beads.

Figures 13A, 13B:
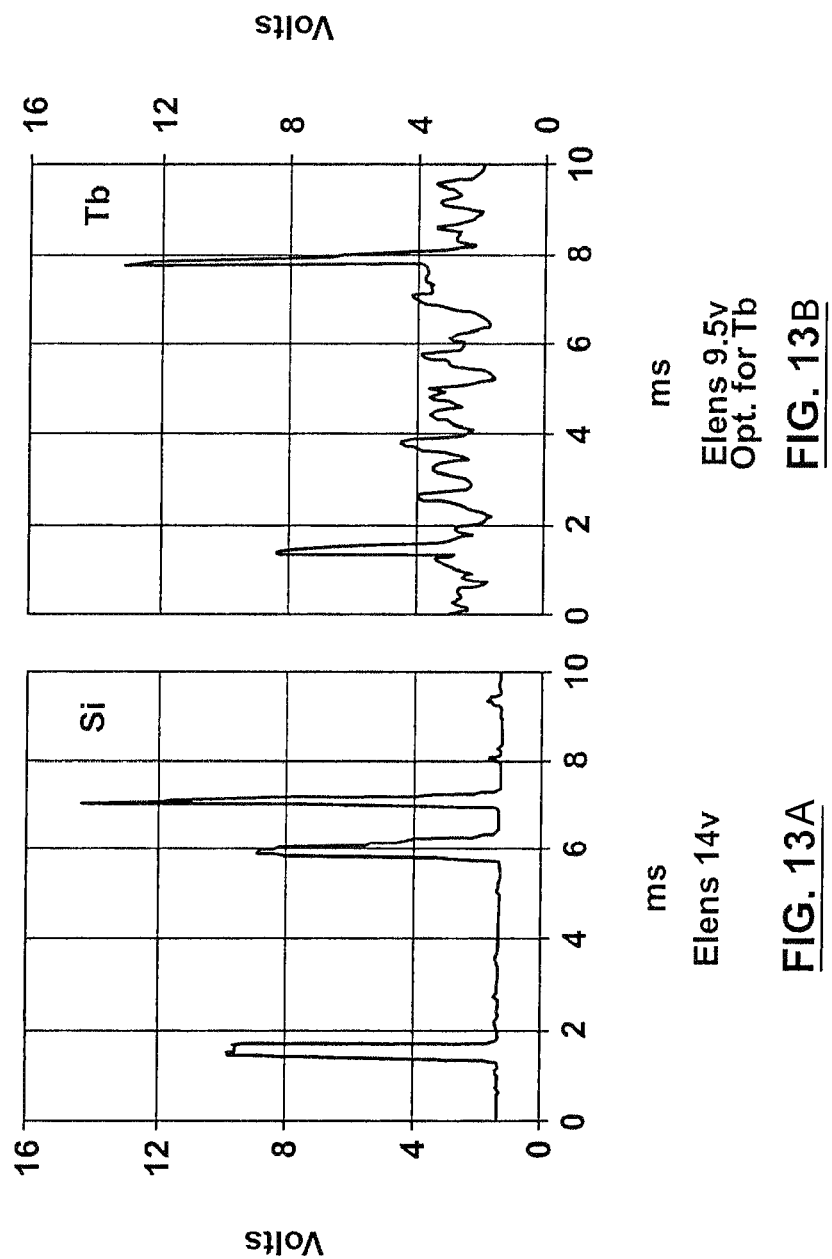
FIG. 13A shows $Si^+$ signal for stober silica particles grown in the presence of a Tb solution.
FIG. 13B shows $Tb^+$ signal for stober silica particles grown in the presence of a Tb solution.

FIGS. 13A and 13B show some of the data obtained. The data provided in FIG. 13A shows the detection of $Si^+$, clearly indicating that the beads are vaporized, atomized and ionized. Data provided in FIG. 13B show the detection of $Tb^+$ (for beads grown in Tb solution). Clearly, the Tb label is detected. If a mixture of beads having different lanthanide labels were sampled, the different lanthanide signals would identify the different beads. It is also evident that beads can be grown in solutions of mixed lanthanides (or other elements), and would incorporate the different elements, thus providing for a larger number of distinguishable beads as indicated above. The availability of a simultaneous analyzer would further allow simultaneous detection of the elements associated with the bead itself and also with the tag associated with a secondary affinity product that recognizes a captured antigen.

Therefore, elements within a bead can be detected (i.e., the bead is vaporized to its atomic components). Different combinations of element internal "labels" can be used to distinguish beads. If those beads carry different surface antibodies to bind different antigens, and those antigens are then recognized by another antibody containing a different element reporter tag, a multiplexed assay is enabled. Alternatively, the differently labeled beads can be used with the same surface antibodies, but with the different beads being applied to different samples (such as a 96 well plate), so that the signal associated with the labeled affinity product identifies the antigen concentration in the sample indicated by the signals corresponding to the bead composition. Numerous modifications, variations and adaptations may be made to the particular embodiments of the invention described above without departing from the scope of the invention, which is defined in the claims.

REFERENCES

The following publications are hereby incorporated by reference
1. Hanayama, R.; Tanaka, M.; Miwa, K.; Shinohara, A.; Iwamatsu, A.; Nagata, S. Identification of a factor that links apoptotic cells to phagocytes. Nature 2002, 417, 182-187.
2. Reif, K.; Ekland, E. H.; Ohl, L.; Nakano, H.; Lipp, M.; Forster, R.; Cyster, J. G. Balanced responsiveness to chemoattractants from adjacent zones determines B-cell position. Nature 2002, 416, 94-99.
3. Heppner, F. L.; Musahl, C.; Arrighi, I.; Klein, M. A.; Rulicke, T.; Oesch, B.; Zinkemagel, R. M.; Kalinke, U.; Aguzzi, A. Prevention of scrapie pathogenesis by transgenic expression of anti-prion protein antibodies. Science 2001, 294, 178-182.
4. Shinkai, K.; Mohrs, M.; Locksley, R. M. Helper T cells regulate type-2 innate immunity in vivo. Nature 2002, 420, 825-829.
5. Marx, J. Mutant stem cells may seed cancer. Science 2003 301: 1308-1310.
6. Lapidot, T. C. Sirard J. Vormoor, B. Mudoch T. Hoang, J. Caceres-Cortes, M. Minden, B. paterson, M. Caligiuri, and J. E. Dick. A cell initiating human acute myeloid leukaemia after transplantation inot SCID mice. Nature 1994 367, 6464: 645-648.
7. Meldrum, D. R.; Holl, M. R. Tech. Sight. Microfluidics. Microscale bioanalytical systems. Science 2002, 297, 1197-1198.
8. Schenk, T.; Molendijk, A.; Irth, H.; Tjaden, U. R.; van der, G. J. Liquid chromatography coupled on-line to flow cytometry for postcolumn homogeneous biochemical detection. Anal. Chem. 2003, 75, 4272-4278.
9. S. D. Tanner. Space charge in ICP-MS: Calculation and implications. Spectromchimica Acta 1992 47B: 809-823.
10. Mazurier, F.; Doedens, M.; Gan, 0. I.; Dick, J. E. Rapid myeloerythroid repopulation after intrafemoral transplantation of NOD-SCID mice reveals a new class of human stem cells. Nat. Med. 2003, 9, 959-963.
11. Quinn, Z. A.; Baranov, V. I.; Tanner, S. D.; Wrana, J. L. Simultaneous determination of proteins using an element-tagged immunoassay coupled with ICP-MS detection. J. Anal. Atom. Spectrom. 2002, 17, 892-896.

What is claimed is:

1. A system for sequentially analyzing single cells in a sample by mass spectrometry,
    wherein the sample comprises a plurality of tagged cells tagged with a plurality of tagged antibodies, wherein each of the plurality of tagged antibodies is specific for a different analyte, and wherein each of the plurality of tagged antibodies is tagged with an elemental tag comprising a lanthanide or noble metal;
    wherein the system comprises:
    a first device to vaporize, atomize, and ionize multiple elemental tags from a single first cell of the plurality of tagged cells and multiple elemental tags from a single second cell of the plurality of tagged cells; and
    a second device to detect, by mass spectrometry, lanthanides and/or noble metals of the single first cell by detecting a transient signal of the multiple vaporized, atomized, and ionized elemental tags of the single first cell, and lanthanides and/or noble metals of the single second cell by detecting a transient signal of the multiple vaporized, atomized, and ionized elemental tags of the single second cell, wherein the transient signal associated with the single first cell and the transient signal associated with the single second cell are detected sequentially.

2. The system of claim 1, wherein the system is further configured to lyse the plurality of tagged cells prior to vaporizing, atomizing, and ionizing the multiple elemental tags from the single first cell.

3. The system of claim 2, wherein the system is further configured to sequentially vaporize, atomize, and ionize fragments of the single first cell.

4. The system of claim 1, wherein system is further configured to sequentially detect fragments of the single first cell.

5. The system of claim 1, wherein at least one of the plurality of tagged antibodies is tagged using diethylenetriaminepentaacetic acid anhydride (DTPA), 1,4,7,10-tetraazacyclododecanetetraacetic acid (DOTA), or a derivative thereof.

6. The system of claim 1, wherein each of the plurality of tagged antibodies is tagged with a distinct isotope.

\* \* \* \* \*